(12) United States Patent
Fuerst et al.

(10) Patent No.: US 11,819,288 B2
(45) Date of Patent: *Nov. 21, 2023

(54) TROCAR POSE ESTIMATION USING MACHINE LEARNING FOR DOCKING SURGICAL ROBOTIC ARM TO TROCAR

(71) Applicant: Verb Surgical Inc., Santa Clara, CA (US)

(72) Inventors: Bernhard A. Fuerst, Sunnyvale, CA (US); Dennis Moses, Hollywood, FL (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 608 days.

This patent is subject to a terminal disclaimer.

(21) Appl. No.: 16/824,588

(22) Filed: Mar. 19, 2020

(65) Prior Publication Data

US 2021/0290311 A1  Sep. 23, 2021

(51) Int. Cl.
*G06F 19/00* (2018.01)
*A61B 34/20* (2016.01)
(Continued)

(52) U.S. Cl.
CPC .......... *A61B 34/20* (2016.02); *A61B 17/3423* (2013.01); *A61B 34/30* (2016.02); *A61B 34/32* (2016.02); *B25J 9/163* (2013.01); *B25J 9/1694* (2013.01); *B25J 13/089* (2013.01); *B25J 19/027* (2013.01); *A61B 90/50* (2016.02);
(Continued)

(58) Field of Classification Search
CPC ..... A61B 34/20; A61B 17/3423; A61B 34/30; A61B 34/32; A61B 90/50; A61B 2034/2051; A61B 2034/302; A61B 2090/571; A61B 17/3421; A61B 90/57; A61B 2034/2048; A61B 2034/2059; B25J 9/163; B25J 9/1694; B25J 13/089; B25J 19/027; B25J 9/1689; G05B 2219/40174

See application file for complete search history.

(56) References Cited

U.S. PATENT DOCUMENTS

2017/0209059 A1* 7/2017 Nabutovsky ........... A61B 5/287
2018/0049824 A1   2/2018 Harris et al.
(Continued)

FOREIGN PATENT DOCUMENTS

JP   2019524284   9/2019
KR   10-2014-0020071   2/2014

OTHER PUBLICATIONS

International Search Report and Written Opinion for International Application No. PCT/US2020/049764 dated Dec. 21, 2020, 13 pages.
(Continued)

*Primary Examiner* — Abby Y Lin
*Assistant Examiner* — Sohana Tanju Khayer
(74) *Attorney, Agent, or Firm* — Aikin & Gallant, LLP

(57) ABSTRACT

A surgical robotic system senses position or orientation of an object, which may be a trocar that has a magnetic field. Magnetic field sensors are coupled to a surgical robotic arm. A machine learning model coupled to the magnetic field sensors is trained to output three-dimensional position and/or three-dimensional orientation of the trocar or other object. Other aspects are also described.

18 Claims, 17 Drawing Sheets

(51) Int. Cl.
  *A61B 17/34*   (2006.01)
  *B25J 9/16*    (2006.01)
  *B25J 13/08*   (2006.01)
  *A61B 34/30*   (2016.01)
  *A61B 34/32*   (2016.01)
  *B25J 19/02*   (2006.01)
  *A61B 90/50*   (2016.01)
  *A61B 90/57*   (2016.01)

(52) U.S. Cl.
  CPC . *A61B 2034/2051* (2016.02); *A61B 2034/302* (2016.02); *A61B 2090/571* (2016.02)

(56) References Cited

U.S. PATENT DOCUMENTS

| | | | |
|---|---|---|---|
| 2018/0289431 A1 | 10/2018 | Draper et al. | |
| 2019/0183585 A1* | 6/2019 | Rafii-Tari | A61B 34/20 |
| 2019/0201104 A1* | 7/2019 | Shelton, IV | G16H 30/40 |
| 2019/0201120 A1 | 7/2019 | Shelton, IV et al. | |
| 2019/0239764 A1* | 8/2019 | Sulkin | A61B 5/6852 |
| 2019/0321115 A1 | 10/2019 | Anderson et al. | |
| 2020/0297292 A1* | 9/2020 | Alexandroni | A61B 6/5294 |
| 2020/0315572 A1* | 10/2020 | Salgaonkar | A61B 8/0883 |
| 2022/0142713 A1* | 5/2022 | Oren | A61B 5/6852 |

OTHER PUBLICATIONS

International Preliminary Report on Patentability for International Application No. PCT/US2020/049764 dated Sep. 29, 2022, 8 pages.

* cited by examiner

Measuring, by a plurality of sensors coupled to a docking interface of a tool drive coupled to the robotic arm, a magnetic field generated by a pair of magnets embedded in the trocar to produce a measured sensor reading, the pair of magnets having a known placement including known positions relative to each other and a known offset of respective axes of polarity between each magnet Selecting, by one or more processors, an initial estimated pose of the trocar, the pose including a position and an orientation of the trocar (e.g., relative to a known pose of the docking interface).

Calculating, by the one or more processors, an estimated sensor reading based on the estimated pose of the trocar, the known placement of the pair of magnets, and a physical model of the sensors.

Computing a difference between the estimated sensor reading and the measured sensor reading.

Is the difference less than a threshold value?

No → Produce an updated estimated pose of the trocar

Yes → Driving the robotic arm such that the docking interface is guided toward the trocar based on the updated estimated pose of the trocar

FIG. 11

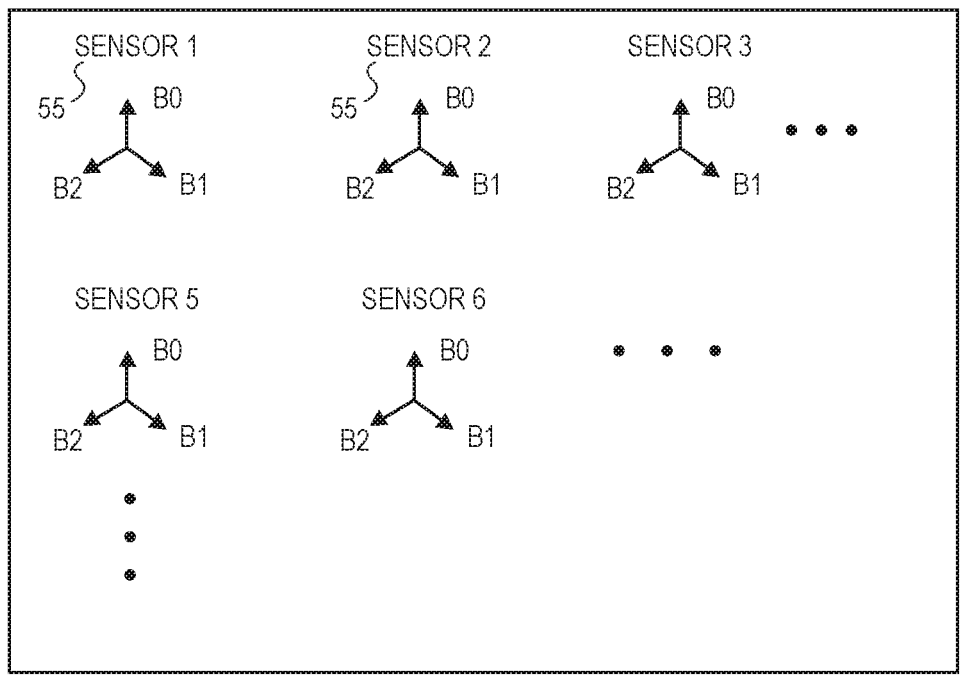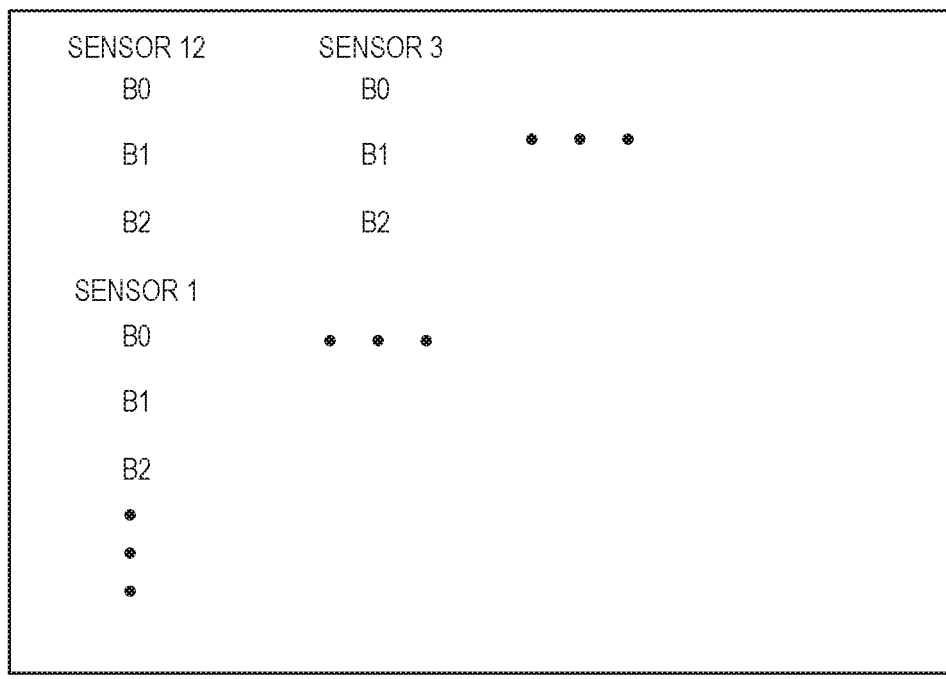
FIG. 14

TROCAR POSE ESTIMATION USING MACHINE LEARNING FOR DOCKING SURGICAL ROBOTIC ARM TO TROCAR

TECHNICAL FIELD

This disclosure relates to techniques for docking a surgical robotic arm to a trocar.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

In MIS procedures, access is provided to the body cavity of a patient through a trocar. Once a distal end of a cannula of the trocar is properly positioned and inserted through tissue and into an interior region of the patient, for example, through the abdominal wall of the patient, a surgical robotic arm having a trocar docking interface at its distal end is manually maneuvered by a user until the interface is adjacent to and aligned with an attachment portion (e.g., a mating interface) on the proximal end of the trocar (outside the patient.) The user then manually latches the arm and trocar docking interfaces to each other, thereby rigidly attaching the arm to the trocar. A surgical tool having an end effector at its distal end (e.g., scissors, grasping jaws, or camera) is then inserted into an outside opening of the cannula, and a transmission housing of the tool is then attached to the arm.

SUMMARY

Applicant has discovered a need for improved systems and methods for docking a surgical robotic arm to a trocar that has been inserted into a patient. Such techniques should obviate the challenges that are presented by some modalities of trocar docking. For example, some trocar docking procedures employ optical tracking through the use of visual imaging sensors that guide the surgical robotic arm to the trocar. However, visual sensors can be blocked by the sterile barriers or drapes that cover the surgical robotic arm and its surrounding environment. Additional examples of trocar docking techniques, for example, ultrasonic triangulation, inertial sensing, and the detection of generated electromagnetic fields, involve the use of electrically powered components on the trocar that generate signals that can be used to guide the robotic arm. However, such electrically powered equipment can reduce the lifespan of a trocar, as these components can degrade, for example, due to repeated use and/or through sterilization procedures.

The use of magnets, for example, non-electrically powered magnets such as permanent magnets, in the trocar can provide magnetic fields for detection by a sensor system in a surgical robotic arm, such that the robotic arm can be controlled to automatically align with a pose of the trocar where it can then be mechanically coupled to the trocar. The use of such magnetic sensing does not require a line-of-sight between the robotic arm and the trocar so that, for example, sterile barriers can be used to cover portions of the robotic arm without interfering with trocar docking procedures. In addition, the use of magnets in the trocar to generate the signals based on which the robotic arm is guided does not require electrically powered components and as such the trocar is more robust having increased lifespan and versatility.

In one embodiment, an arm-to-trocar docking capability of a surgical robotic system senses position, orientation or both (pose) of the trocar. The surgical robotic system includes a surgical robotic arm, magnetic field sensors on the arm, and a digital processor that implements a machine learning model (e.g., an artificial neural network "neural network"). The machine learning model is coupled to receive output data of the magnetic field sensors. The machine learning model is trainable to output a three-dimensional sensed position, a three-dimensional sensed orientation, or both (sensed pose, in six degrees of freedom), of a trocar that is producing a magnetic field. The sensing of three-dimensional position or orientation of the trocar is thus based on output data from the trocar-mounted magnetic field sensors that propagates through the machine learning model. In one version, the surgical robotic system performs a digital algorithm that automatically drives the motorized joints of the surgical robotic arm to guide the docking interface on the arm to dock with the trocar, based on its sensed position or orientation (e.g., both, as pose) of the trocar.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

FIG. 11 is a process flow for docking a tool drive attached to a robotic arm of a surgical robotic system to a trocar according to one aspect of the disclosure.

FIG. 14 illustrates a two-dimensional physical array of sensors and a two-dimensional array of sensor output data elements, which are suitable for input to the machine learning model of FIG. 13 (for use as part of the surgical robotic system of FIG. 12.)

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
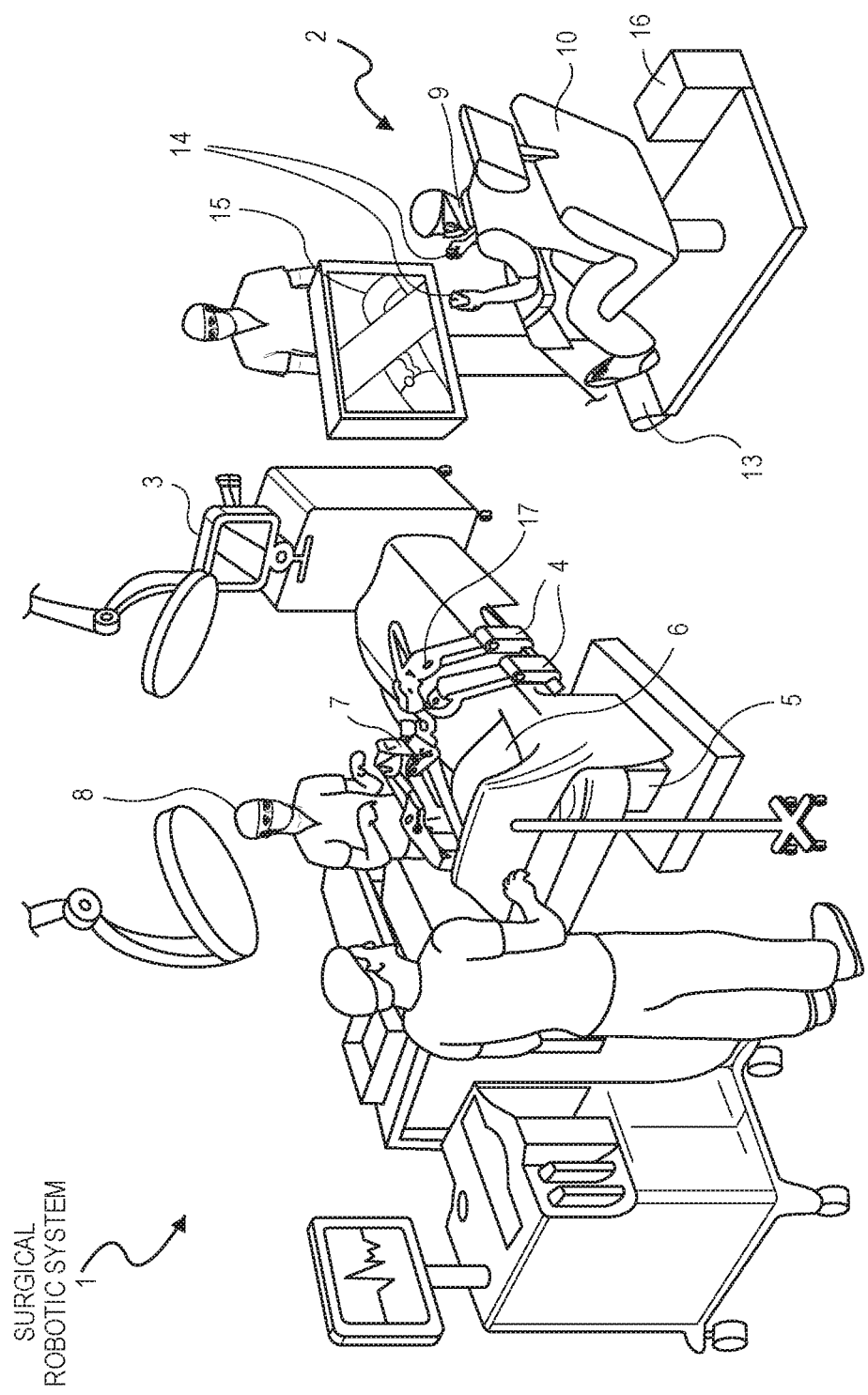
FIG. 1 is an overview schematic of an operating room arrangement with a surgical robotic system.

Referring to FIG. 1, this is a pictorial view of an example surgical robotic system 1 in an operating arena. The robotic system 1 includes a user console 2, a control tower 3, and one or more surgical robotic arms 4 that may be mounted to a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

To create a port for enabling introduction of a surgical instrument into the patient 6, a trocar assembly may be at least partially inserted into the patient through an incision or entry point in the patient (e.g., in the abdominal wall). The trocar assembly may include a cannula or trocar 63 (FIG. 5), an obturator, and/or a seal. In some variations, the trocar assembly can include an obturator such as a needle with a sharpened tip for penetrating through a patient's skin. The obturator may be disposed within the lumen of the trocar 63 when being inserted into the patient 6, and then removed from the trocar 63 such that a surgical instrument may be inserted through the lumen of the trocar 63. Once positioned within the body of the patient 6, the trocar 63 may provide a channel for accessing a body cavity or other site within the patient 6, for example, such that one or more surgical instruments or tools can be inserted into a body cavity of the patient 6, as described further herein.

Figure 2:
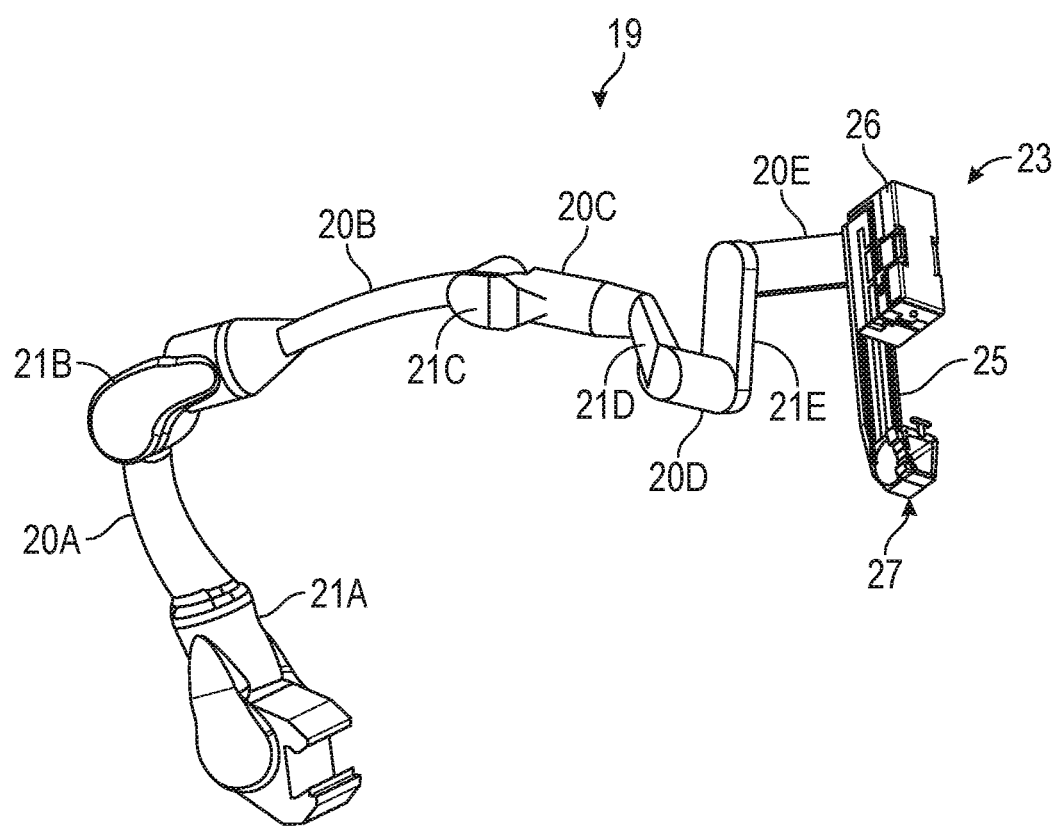
FIG. 2 is a perspective view of a portion of a robotic arm according to one aspect of the disclosure.

Turning to FIG. 2, a portion of a robotic arm 19 is illustrated according to an exemplary embodiment of the disclosure. The robotic arm 19 and associated components described herein can form a surgical robotic assembly 21 according to an exemplary embodiment of the disclosure. The surgical robotic assembly 21 can be incorporated into the surgical robotic system 1 described above, or can form a portion of a different system. The robotic arm 19 can include a plurality of links and a plurality of actuated joint modules that enable relative movement between adjacent links. While a single robotic arm 19 has been illustrated, it will be understood that the robotic arm 19 can include additional arm portions or can be a component of a multi-arm apparatus without departing from the disclosure.

The robotic arm 19 can include a plurality of links (e.g., links 20A-20E) and a plurality of joint modules (e.g., joints 21A-21E) for actuating the plurality of links relative to one another. The joint modules can include various joint types, such as a pitch joint or a roll joint, any of which can be actuated manually or by the robotic arm actuators 17, and any of which may substantially constrain the movement of the adjacent links around certain axes relative to others. As also shown, a tool drive 23 is attached to the distal end of the robotic arm 19. As described herein, the tool drive 23 can be configured with a docking interface 27 to receive and physically latch or lock with an attachment portion (e.g., a mating interface) of a trocar 63 such that one or more surgical instruments (e.g., endoscopes, staplers, etc.) can be guided through a lumen of the cannula of the trocar 63. The plurality of the joint modules 21A-21E of the robotic arm 19 can be actuated to position and orient the tool drive 23 for robotic surgeries.

Figure 3:
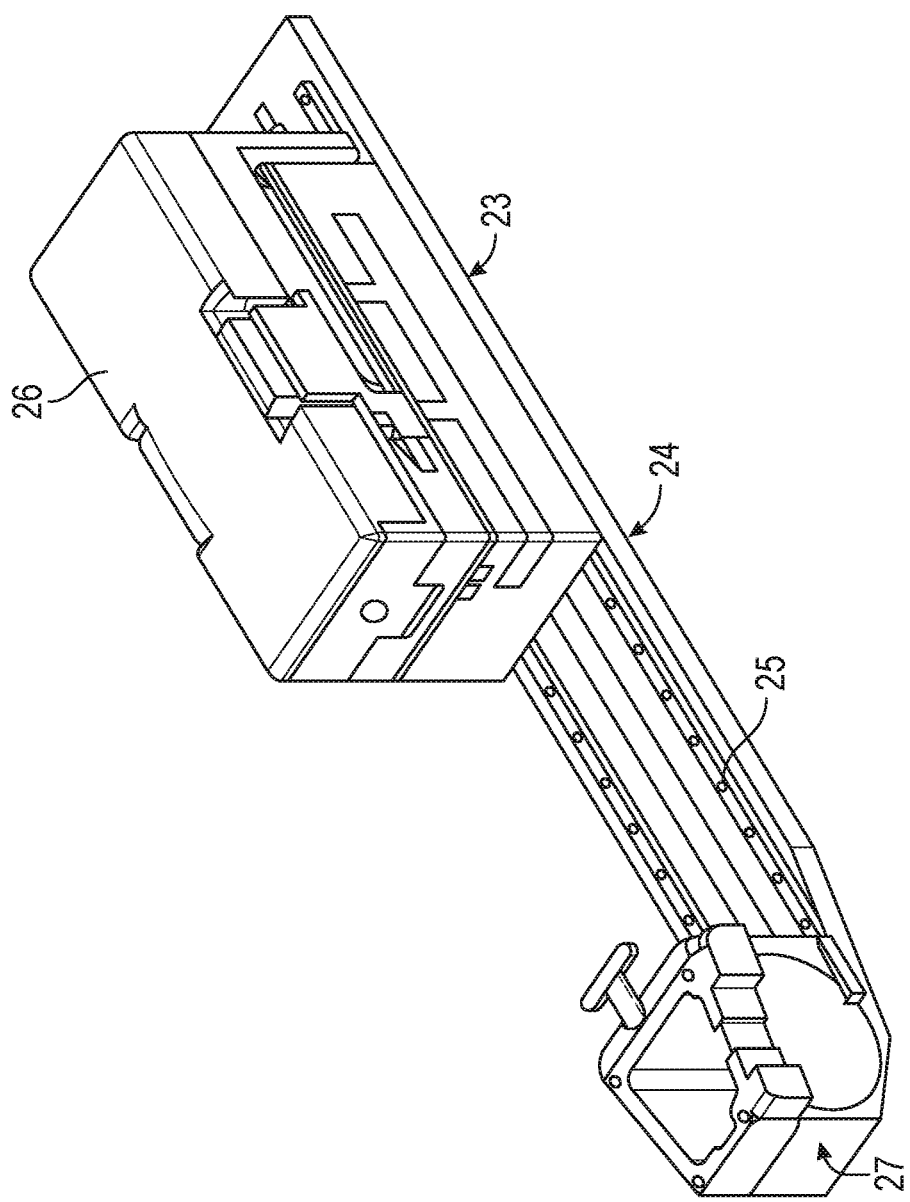
FIG. 3 is a schematic perspective view of a tool drive of the robotic arm of FIG. 2.

FIG. 3 is a schematic diagram illustrating an exemplary tool drive 23 without a loaded tool, in accordance with aspects of the subject technology. In one variation, the tool drive 23 may include an elongated base (or "stage") 24 having longitudinal tracks 25 and a tool carriage 26, which is slidingly engaged with the longitudinal tracks 25. The base 24 may be configured to couple to the distal end of a robotic arm 19 such that articulation of the robotic arm 19 positions and/or orients the tool drive 23 in space. The tool carriage 26 may be configured to receive a base of a tool whose elongated portion has been inserted into and extend through the trocar 63. The tool carriage 26 may actuate a set of articulated movements of the tool through a cable system or wires manipulated and controlled by actuated drives (the terms "cable" and "wire" are used interchangeably throughout this application). The tool carriage 26 may include different configurations of actuated drives, such as a mechanical transmission.

The tool drive 23 is configured to receive different surgical tools (e.g., surgical tool 7, as well as other detachable surgical tools—not shown) that can be selectively attached, either one at a time or in combination. Such surgical tools can be, for example, jaws, cutting tools, an endoscope, spreader, implant tool, energy emitter, etc. In this regard, the tool drive 23 can include one or more drive disks and/or other adapters that interface with and engage portions of the surgical tools that are attached thereto. The drive disks are actuatable, for example, through a mechanical transmission in the tool drive 23, to transfer force or torque to the drive disks 29 to effect operation of the attached surgical tool.

Figure 4:
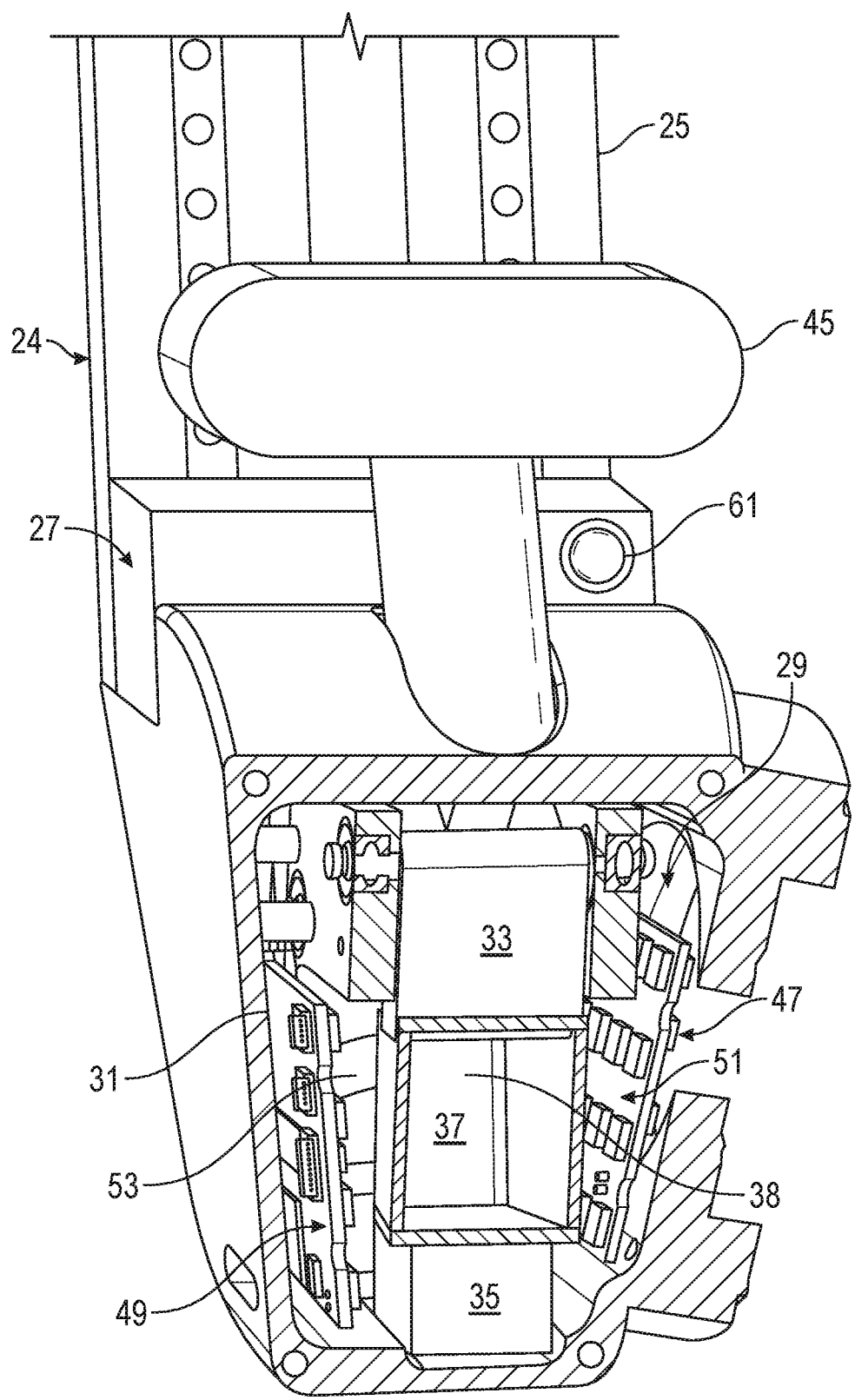
FIG. 4 is a perspective view of a docking interface of the tool drive of FIG. 3.

Referring now to FIG. 4, an example of a docking interface 27 that is coupled to the base 24 of a tool drive 23 is shown. The trocar 63 can be coupled to the tool drive 23 or to another location on the arm 19 at the docking interface 27. The docking interface 27 in this example is located at a distal block of the elongated base 24—see also FIG. 3. The docking interface 27 is configured to receive a portion of the trocar 63 such that the docking interface 27 is configured as a trocar docking interface, a trocar attachment device, or a trocar mounting device. The docking interface 27 can provide a reliable and quick way to removably attach the trocar 63 to the arm 19.

The docking interface 27 can define a chamber 29 that is accessible through a mouth or frontal opening 31 of the docking interface 27 and which can include first and second clamp components 33, 35 (e.g., arms, plates, levers, members) arranged about a receiver 37 that defines a receiving space 38 for receiving a portion of the trocar 63 (e.g., a mating interface formed in an attachment portion of a cannula located in a proximal portion of the cannula). At least one of the clamp components 33, 35 may be pivotable between an open position and a closed position such that an attachment portion 69 of the trocar 63 can be inserted into the receiving space 38 between the clamp components 33, 35 so that a portion of the trocar 63 is held in place at least partially by the first and second clamp components 33, 35.

In one variation, the docking interface 27 may include an over-center mechanism such as a lever 45 or other suitable locking component that mechanically cooperates with the clamp component 33, for example, through a pin and slot arrangement or through another pivotable or movable connection, between the open and closed positions. The lever 45 can be movable, e.g., along a track or slot defined in a body or housing of the docking interface 27, between a forward, locked position (e.g., a locked over-center position) and a rearward, unlocked position. When the lever 43 is moved toward the locked position, the lever 45 may urge the clamp component 33 downwardly toward the receiving space 38 and lock the clamp component 33 in the closed position such that a portion of the trocar 63 is securely held between the first and second clamp components 33, 35. In some variations, second clamp component 35 can be stationary or can be fixed. In one variation, the lever 45 can be controlled and/or driven with an electric motor or actuator under manual or processor control.

In some variations, the docking interface 27 may also provide a sterile barrier between sterile components such as the trocar 63 and non-sterile components such as the first and second clamp components 33, 35 (or other non-sterile components of the surgical system). The sterile barrier may be provided, for example, by a sterile adapter formed of a surgical-grade polymer or other surgical-grade material that is interposed between the trocar 63 and the first and second clamp components 33, 35 (not shown for clarity of illustration).

Figure 5:
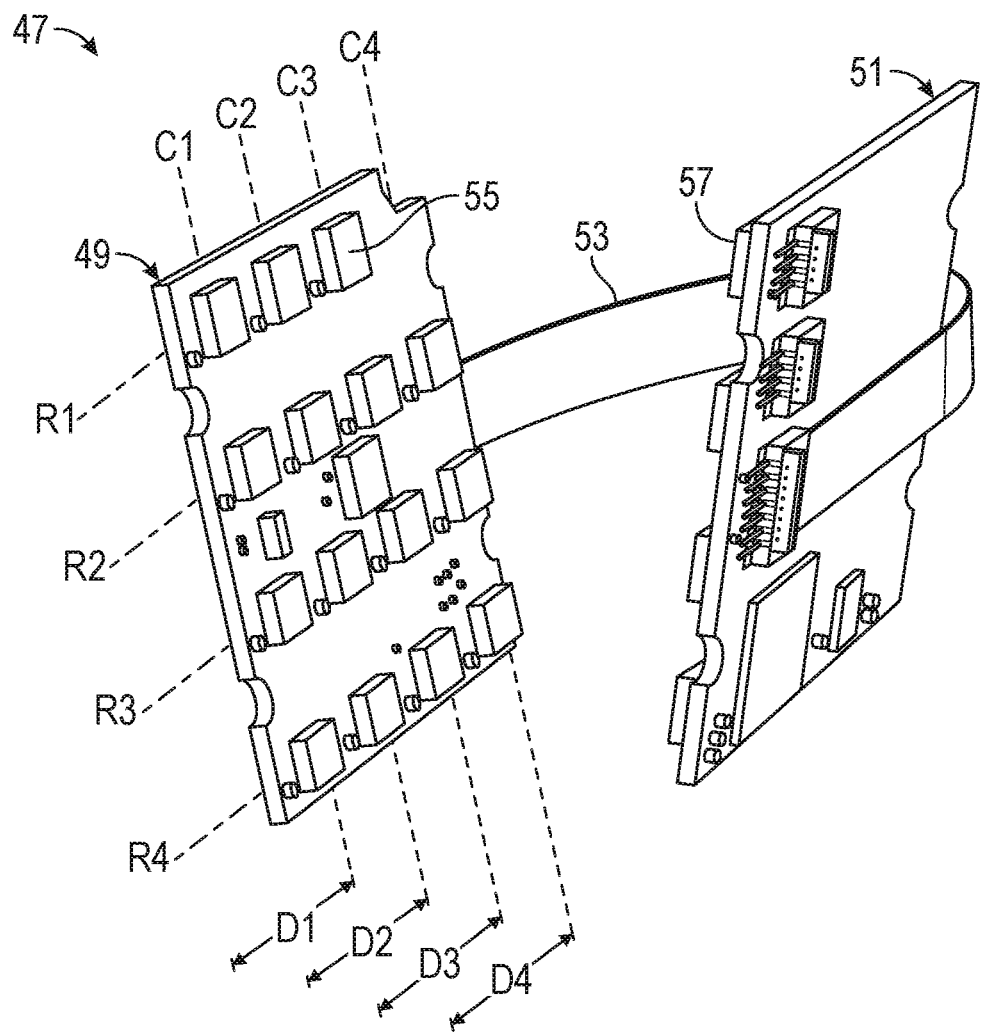
FIG. 5 is a perspective view of a sensor system of the docking interface of FIG. 4.
Figure 6:
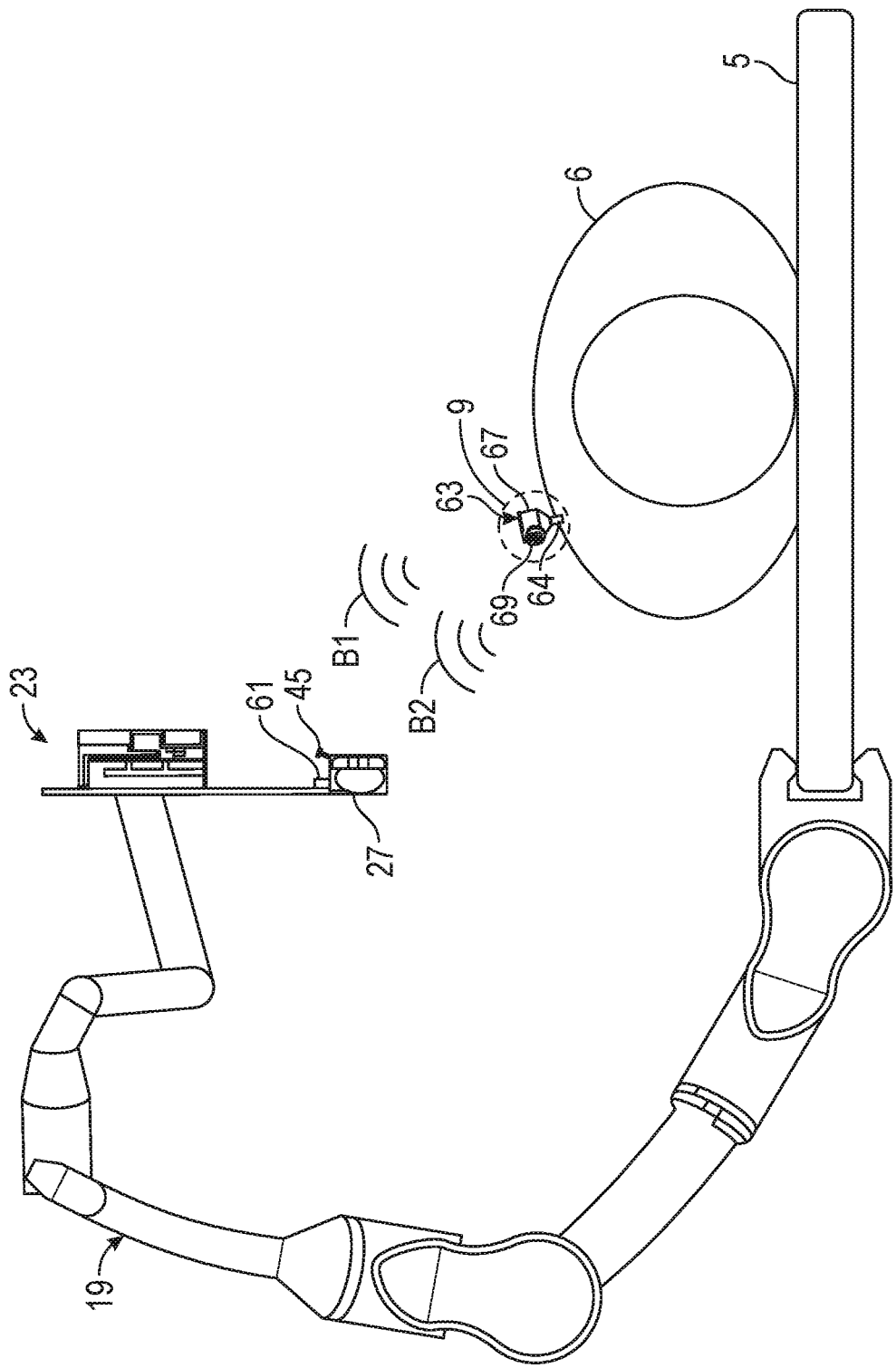
FIGS. 6-8 are pictorial views of operations of a method of docking a tool drive attached to a robotic arm of a surgical robotic system to a trocar according to one aspect of the disclosure.

Referring additionally to FIG. 5, the docking interface 27 also includes a sensor system 47 that includes at least a motherboard or first sensor board 49 at a first location of the docking interface 27 and a daughterboard or second sensor board 51 at second location of the docking interface 27 and in electrical communication with the first sensor board 49 via a cable 53 or other electrically conductive connection. In one variation, communication between the sensor boards 49, 51 can employ a multi-slave and multi-master inter-integrated communication computer bus. One or both of the sensor boards 49, 51 can include a microprocessor or other associated processor, for example, to control and/or read the sensors of the sensor boards 49, 51 and to facilitate communication between the sensor boards 49, 51, e.g., to enable temporal synchronization between the sensor boards 49, 51. As shown, the first sensor board 49 and the second sensor board 51 are positioned spaced apart from but parallel to each other, e.g., facing each other, on opposite lateral sides of the chamber 29 of the docking interface 27. The first sensor board 49 includes a first plurality of sensors 55 and the second sensor board 51 includes a second plurality of sensors 57. In this regard, the sensors 55, 57 are embedded in or otherwise coupled to the robotic arm 19 or the tool drive 23. Each of the plurality of sensors 55, 57 are arranged such that at least one sensor 55, 57 is disposed rearward, e.g., at a depth measured from the frontal opening 31 of the docking interface 27, with respect to another respective sensor 55, 57. As shown, sensors 55, 57 are disposed at least at a first depth D1, a second depth D2, a third depth D3, and a fourth depth D4, with D4>D3>D2>D1. The depths D1, D2, D3, D4 can be spaced at uniform or non-uniform increments without departing from the disclosure. While the sensors 55, 57 have been described in a grid-like configuration of rows R1-R4 and columns C1-C4, it will be understood that one or both of the pluralities of sensors 55, 57 can have a different arrangement without departing from the disclosure.

As described further herein, the sensors 55, 57 are operable to sense or measure a magnetic field associated with the trocar 63, and produce respective corresponding electrical signals. In this regard, the sensors 55, 57 can be configured as magnetometers, e.g., sensors that receive at least a portion of a magnetic field as an input and produce an output electrical signal corresponding to a strength or other characteristic of the magnetic field, and such that the sensors 55, 57 can be transducers. Any of the sensors 55, 57 can be configured to receive a different physical input and produce a corresponding electrical signal, for example, inertial measurement units, accelerometers, etc. In this regard, the sensors 55, 57 produce an output electrical signal that can be electrically communicated to, for example, a processor or controller that is incorporated into the control tower 3 to provide force or velocity commands to guide (e.g., direct a movement of) the robotic arm 19 via the robotic arm actuators 17, as described further herein. It will be understood that a processor can be incorporated into additional or alternative portions of the surgical robotic system 1, and that the sensor system 47 can be in electrical communication with one or more different processors. A switch 61 or other control is mounted on or near the docking interface 27, for example, behind the lever 45 at a position such that the lever 45 can be urged into contact with the switch 61, as described further herein. The switch 61 can be in electrical communication with the processor in the control tower 3 to signal the processor to energize or activate one or both of the sensor boards 49, 51 to activate the sensor system 47 to sense or measure magnetic fields, and to effect guidance of the robotic arm 19 toward the trocar 63 according to an algorithm, as described further herein. In one variation, the sensor system 47 can be activated by the processor prior to or independently of the action of the switch 61, and the switch 61 can be used to signal the processor to begin calculations based on the signals received from the sensor system 47 to determine the estimated pose of the trocar and then affect guidance of the robotic arm 19 and its coupled tool drive 23. The switch 61 can be have one of several different configurations, e.g., a mechanical button and mechanical switch combination may be preferred but another form of tactile interface or a touchscreen is also possible, that can be activated by a user. Such placement of the switch 61 on or near the docking interface 27 allows an operator to activate a docking process without the need to travel away from the robotic arm 19 to a separate control interface, for example, the user control 2 that is located away from the robotic arm 19/tool drive 23.

While the sensor boards 49, 51 have been generally described as respective first and second printed circuit boards (PCBs) including the respective sensors 55, 57 embedded therein or thereon, it will be understood that the sensor system 47 can be provided in a different arrangement, for example, as discrete components, without departing from the disclosure. Additionally, it will be understood that any of the components described herein can be in communication via wired and/or wireless links, using any suitable ones of a variety of data communication protocols.

Referring additionally to FIGS. 6-9, guidance and docking of the docking interface 27 of the tool drive 23 with a trocar 63 that is at least partially inserted into the patient 6 is illustrated according to one aspect of the disclosure. The trocar 63, as shown, includes a generally tubular body 64 with a flanged upper portion or head 67 and an attachment portion 69 that protrudes from the head 67 for mating with the docking interface 27. In one variation, the attachment portion 69 can be configured, for example, as having a nose or collar or pin-like arrangement, and can have one or more surface features, e.g., notches, ridges, protrusions, angles, hooks, etc., for interengaging the receiver 37 of the docking interface 27.

The trocar 63 can have a different arrangement without departing from the disclosure. The trocar 63 includes a first magnet 71 and a second magnet 73 producing respective magnetic fields B1, B2 with known properties, e.g., known axes of polarization or angles therebetween, known dipole moments, known positions with respect to each other, etc. The first magnet 71 and the second magnet 73 each can have a different axis of polarization, e.g., an axis extending between opposite poles of the respective magnets 71, 73. In this regard, the first magnet 71 and the second magnet 73 may be obliquely arranged relative to one another, e.g., such that an angle is disposed between the respective axes of polarization. One or both of the magnets 71, 73 can be embedded in or otherwise coupled to the trocar 63, for example, by being integrally molded therein, by being inserted into a receiving portion thereof, or by being otherwise secured to the trocar 63. In one variation, the magnets 71, 73 are integrally formed in the attachment portion 69 of the trocar 63. In other variations, the magnets 71, 73 can be coupled to or embedded in a different portion of the trocar 63. While the trocar 63 is described as having the pair of magnets 71, 73, it will be understood that the trocar 63 can have a different number of magnets, e.g., provided as multiple pairs or singly-arranged magnets, without departing from the disclosure. In one variation, the trocar 63 can include a single magnet.

Still referring to FIGS. 6-9, and with additional reference to the process flows of FIGS. 10 and 11, a method for docking the robotic arm 19 to the trocar 63 according to aspects of the disclosure will be described and shown. The robotic arm 19 and docking interface 27, in a first or parked or unknown pose, is a pose in which the docking interface 27 is positioned a distance away from the magnets 71, 73 in the attachment portion 69 of the trocar 63 and respective magnetic fields B1, B2 generated therefrom such that a closer distance between the docking interface 27 and the trocar 63 is desirable to facilitate effective receipt or sensing of the magnetic fields B1, B2 by the sensors 55, 57. The parked or unknown pose of the robotic arm 19 can be, for example, a stowed arrangement of the robotic arm 19.

The docking interface 27 can be directed, guided, or driven to a second or entry position that is proximate, but physically separate from, the trocar 63, for example, manually by an operator (e.g., such that the robotic arm 19 is manually forced or manually guided by the hand of the operator) or via the robotic arm actuators 17. A suitable proximity of the docking interface 27 relative to the trocar 63 in which the sensors 55, 57 of the sensor system 47 can effectively sense or measure the magnetic fields B1, B2 can be indicated, for example, with an audible beep or audible alarm, an indicator light or other visual indicia, or a tactile indicator such as haptic or vibratory feedback on a portion of the robotic arm 19 or tool drive 23. In this regard, the sensors 55, 57 can be activated by the processor, for example, upon an initial setup or preparation of the robotic arm 19 and the tool drive 23, or via an input by an operator, prior to positioning of the robotic arm 19/tool drive 23 at the entry position. As shown at block 103, if the docking interface 27 is not in suitable proximity to the sensor system 47 to effectively sense the magnetic fields B1, B2, e.g., at the entry pose, the robotic arm 19 can be further guided toward the trocar 63, for example, by manual forcing or guidance by the operator, automatically under control of the processor, or some combination thereof, until determination by the processor that the docking interface 27 is positioned to effectively sense the magnetic fields B1, B2.

Figure 7:
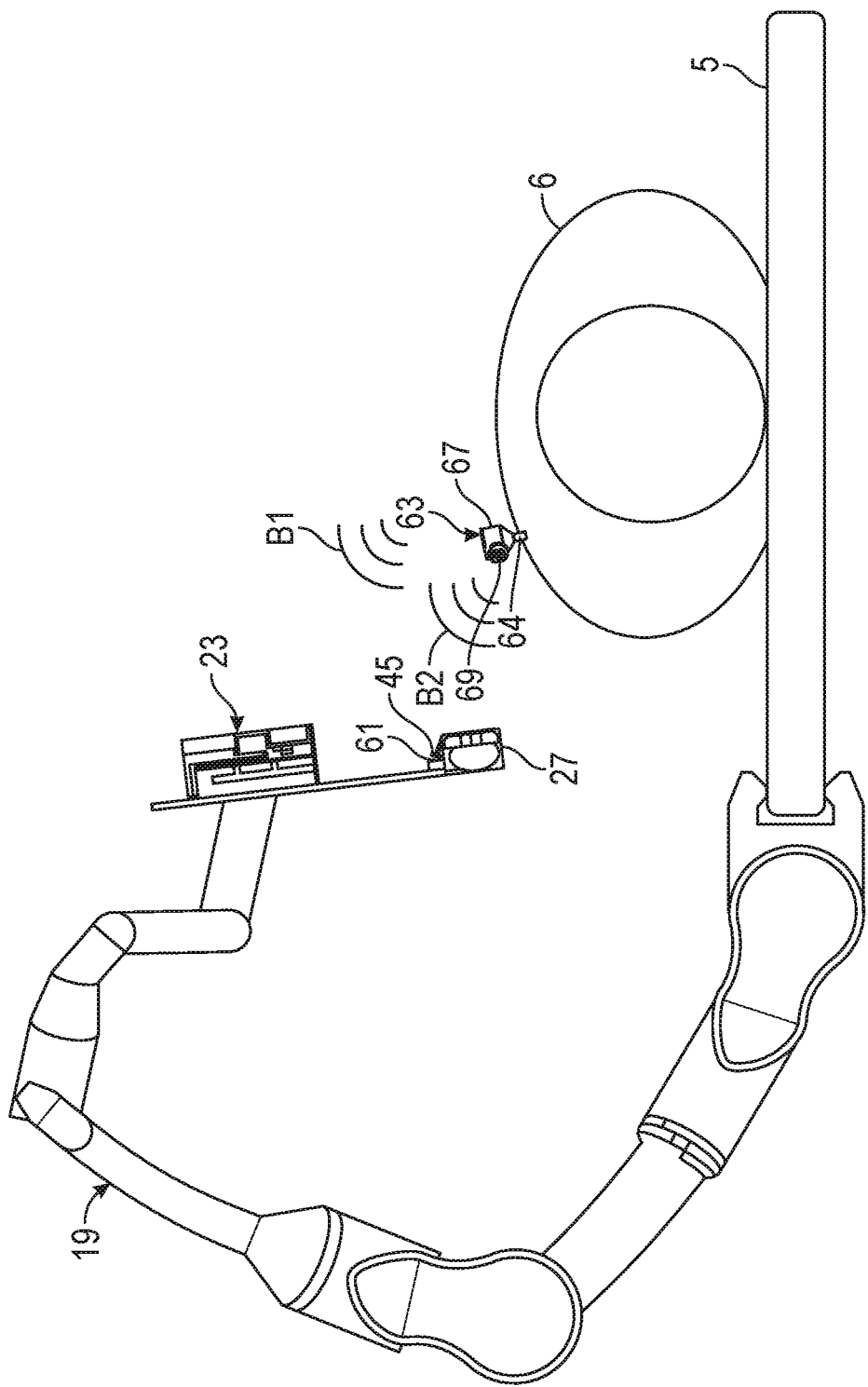
Figure 8:
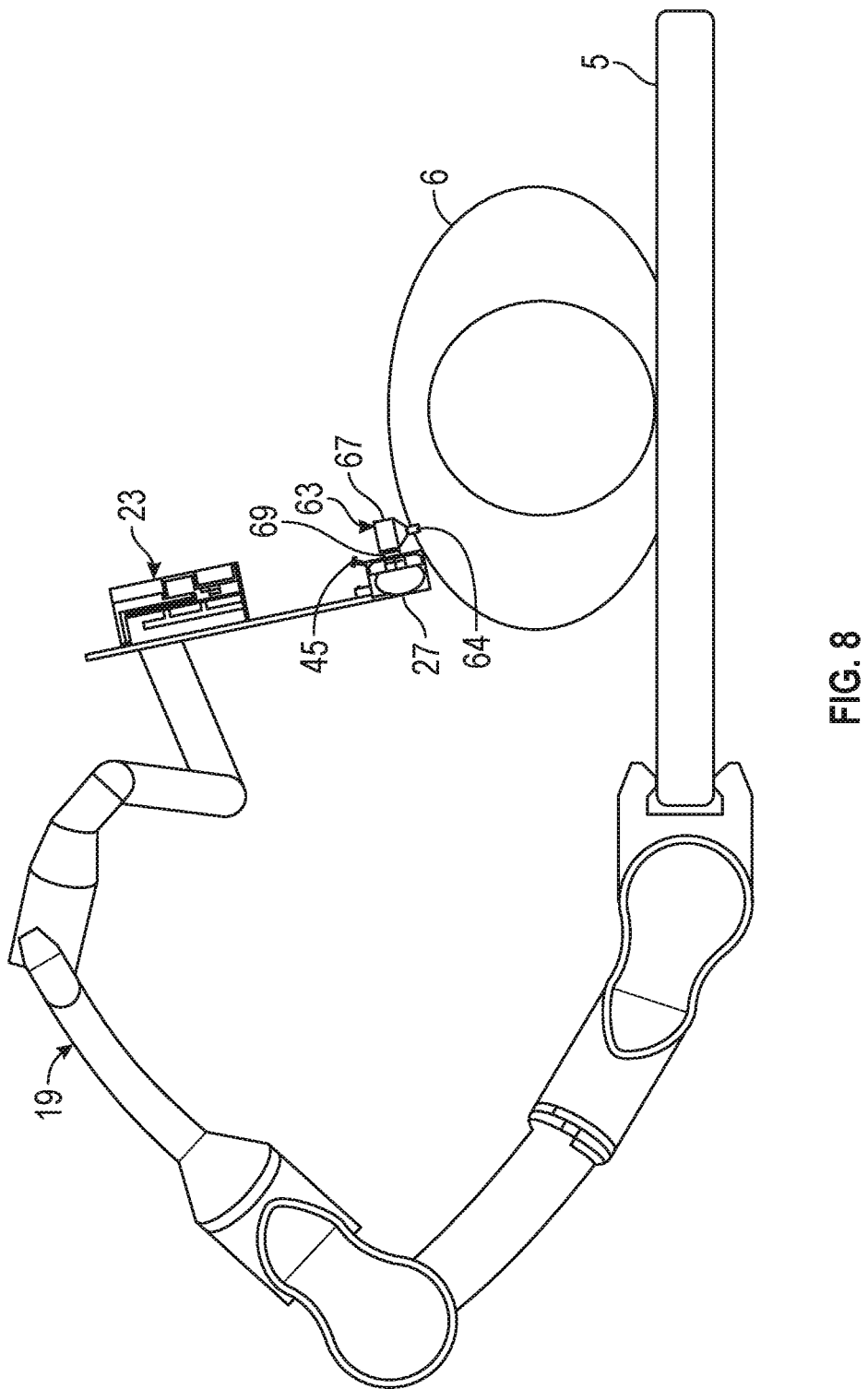
Figure 9:
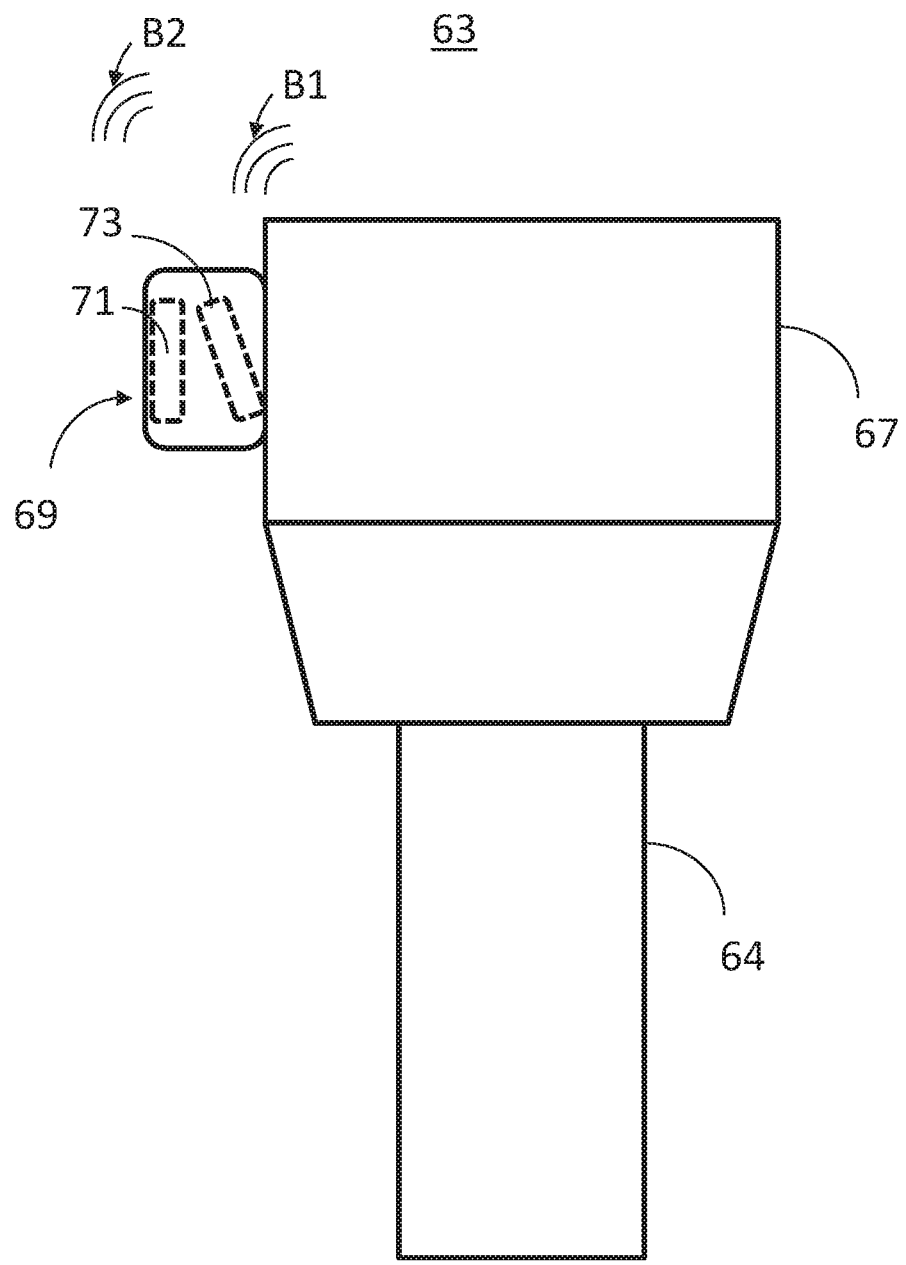
FIG. 9 is an enlarged schematic of the area 9 identified in FIG. 6.

In the entry position shown in FIG. 7, the sensors 55, 57 of the sensor system 47 can sense the magnetic fields B1, B2 emanating from the trocar 63 and produce corresponding electrical signals that are communicated to the processor in the control tower 3. At such positioning of the robotic arm 19/docking interface 27 at the entry position, the processor can begin to calculate a position and orientation of the trocar 63 relative to the docking interface 27 based upon signals received from the sensor system 47 according to an algorithm. The initialization or start of such algorithm can be prompted, for example, by activating the switch 61. In one variation, the switch 61 can be activated by moving the lever 45 rearwardly into the unlocked (rearward) position such that the lever 45 contacts and actuates the switch 61.

Figure 10:
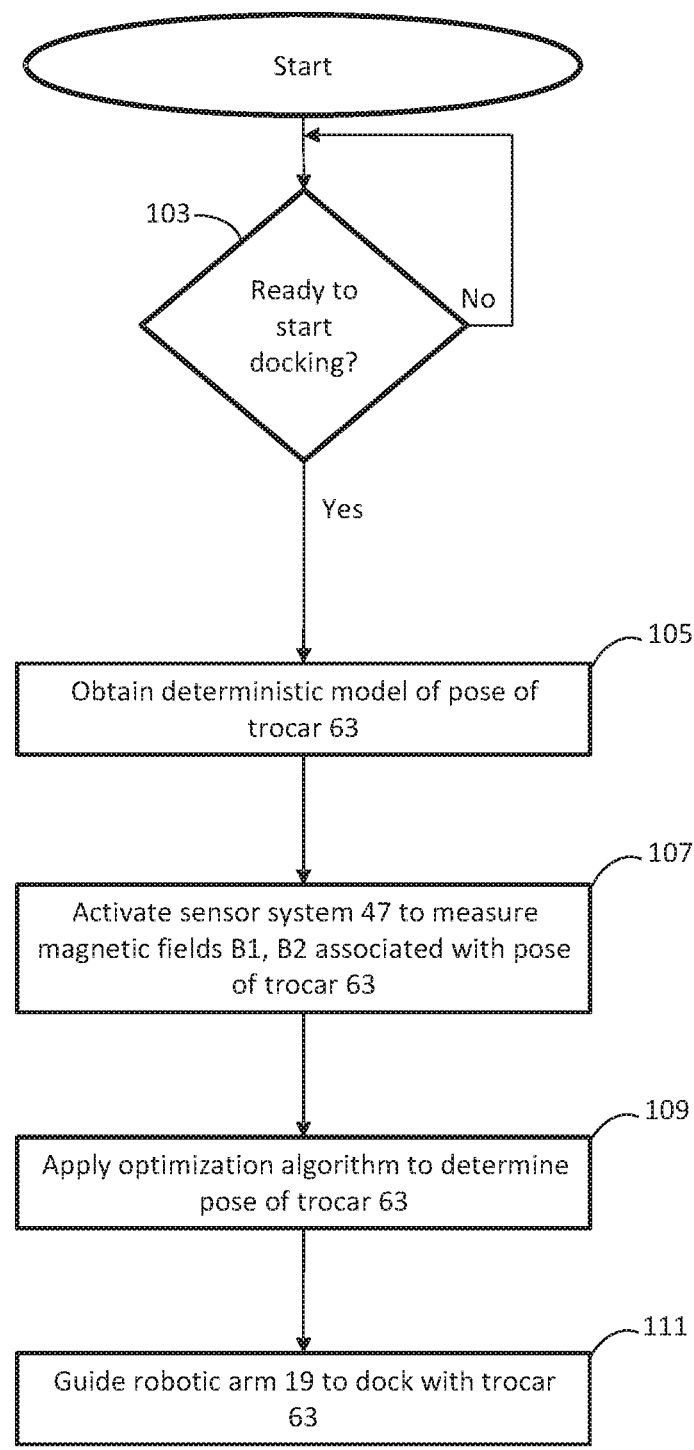
FIG. 10 is a process flow of a method for docking a tool drive attached to a robotic arm of a surgical robotic system to a trocar using a physical/deterministic model of a magnetic field based sensor system.

Accordingly, and with reference to block 107 in FIGS. 10 and 11, the processor in the control tower 3 is signaled by the switch 61 to apply an algorithm to determine the pose, e.g., spatial position and orientation, of the attachment portion 69 of the trocar 63 relative to the docking interface 27 to provide a transform, e.g., a transformation matrix, that can be used to guide or drive the robotic arm 19, and the docking interface 27 of the tool drive 23 attached thereto, toward the trocar 63. Such algorithm or set of algorithms can be a set of computer-implemented instructions, e.g., as part of a computer program product, firmware, etc., that can be stored on a non-transitory computer-readable medium for processing by a processor of the control tower 3, and will be collectively referred to as an algorithm herein. The initialization of the algorithm by the processor can be considered a start of a docking procedure of the robotic arm 19/tool drive 23.

In one variation, and according to the algorithm, the processor in the control tower 3 measures a sensed pose of the attachment portion 69 of the trocar 63 with respect to a 3-axis coordinate system, such as a system of X-, Y-, and Z-axes, by measuring and coordinating the electrical signals output by the sensors 55, 57 of the sensor system 47 to determine the relative strength of the magnetic fields B1, B2 of the respective magnets 71, 73 received at different locations, e.g., depths D1, D2, D3, D4, on the sensor boards 49, 51. For example, if the sensors 55, 57 in the column C1 output electrical signals corresponding to the received magnetic fields B1, B2 that is greater than the output electrical signals of the sensors 55, 57 in the column C2, a determination of a depth distance, e.g., an X-axis location, between the attachment portion 69 of the trocar 63 and the docking interface 27 can be calculated. Similarly, if the sensors 55, 57 in the row R1 output electrical signals corresponding to the received magnetic fields B1, B2 that is greater than the output electrical signals of the sensors 55, 57 in the columns R2, a determination of a vertical distance, e.g., a Z-axis location, between the attachment portion 69 of the trocar 63 and the docking interface 27 can be calculated. Furthermore, if the sensors 55 on the sensor board 49 output electrical signals corresponding to the received magnetic fields B1, B2 that is greater than the output electrical signals of the sensors 57 on the sensor board 51, a determination of a horizontal distance, e.g., a Y-axis location, between the attachment portion 69 of the trocar 63 and the docking interface 27 can be calculated. In one example, as the docking interface 27 is guided or driven along the one or more of the X-axis, the Y-axis, and the Z-axis, the generation of electrical signals by the sensors 55, 57 at the different depths D1, D2, D3, D4 can be used to determine when the trocar 63 becomes closer to the docking interface 27. In this regard, relative saturation of one or more of the sensors 55, 57 by the magnetic fields B1, B2, or degrees thereof, at different locations in the docking interface 27 can be used to determine the relative proximity of the docking interface 27 to the trocar 63.

The generation of differential electrical signals of sensors 55, 57 in different rows R1-R4 and different columns C1-C4 of the sensor boards 49, 51 can also be used by the processor in the control tower 3 to determine rotation about two or more of the X-, Y-, and Z-axes, e.g., roll, pitch, and yaw. For example, in the case of an asymmetrical relative saturation of the sensors 55, 57 by the magnetic fields B1, B2, e.g., such that the docking interface 27 is at least partially tilted with respect to the trocar 63, an orientation of the attachment portion 69 of the trocar 63 with respect to at least two of the X-, Y-, and Z-axes can be determined. In addition, the generation of electrical signals by the sensors 55, 57 can be compared by the processor to the known offset of the axes of polarization of the magnets 71, 73 to determine the rotation of the orientation of the attachment portion 69 of the trocar 63 about another of the X-, Y-, and Z-axes. In this regard, the arrangement of the sensors 55, 57 provides the processor in the control tower 3 with electrical signals corresponding to the magnetic fields B1, B2 according to the algorithm such that a real or sensed pose of the attachment portion 69 of the trocar 63 relative to the docking interface 27 can be determined with respect to six degrees of freedom (DOF): X-axis position, Y-axis position, Z-axis position, X-axis rotation, Y-axis rotation, and Z-axis rotation. In one variation, at least six measurements from the sensors 55, 57 can be used to determine the pose of the trocar 63. The accuracy and precision of the determination of the pose of the trocar 63 may correspond to a number of sensors 55, 57 that are employed in the sensor system 47 such that a desired number of sensors can be selected for use in the sensor system 47.

According to the algorithm, the processor in the control tower 3 can determine the sensed or measured pose of the trocar 63 based on the electrical signals produced by the sensors 55, 57 as described above. It will also be understood that the sensors 55, 57 on respective separate boards 49, 51 can provide comparable electrical signals corresponding to the magnetic fields B1, B2, for example, to reduce error such as electromagnetic noise provided by components of the surgical robotic system 1, for example, motors, actuators, displays, etc. Furthermore, one or more of the boards 49, 51 can incorporate inertial measurement units, for example, to compensate for the magnetic field of the Earth or vibrations of the robotic arm 19, such that associated motions of the robotic arm 19 that are not controlled by the algorithm can be minimized, inhibited, or prevented.

It will be understood that references to the pose of the trocar 63 herein are relative, specifically, to the sensor boards 49, 51 of the sensor system 47 that are mounted in the docking interface 27 of the tool drive 23. In this regard, an arrangement of the sensor boards 49, 51 relative to the surrounding docking interface 27 may be taken into account in determinations of the pose of the docking interface 27 described herein.

Physical/Deterministic Model Based Estimation of Trocar Pose

In one embodiment, the algorithm applied by the processor in the control tower 3 to produce estimated sensor readings are output from a physical or deterministic model of the sensor system 47, e.g., a deterministic model of a position and arrangement of the sensor boards 49, 51 (see block 105 of FIG. 10). Such deterministic model of the sensor system 47 can be provided by the processor in the presence of a virtual representation of the magnetic fields B1, B2 that is modeled on the known properties of the magnets 71, 73, and which include the known relative offset of the respective axes of polarization of the magnets 71, 73. Accordingly, the deterministic model can be obtained or otherwise available to the processor (block 105 in FIG. 10) prior to the start of the algorithm described herein.

Such deterministic model can be a pre-defined function or set of functions applied by the processor that receive, as an input, an estimated pose of the trocar 63 relative to the modeled sensor system 47, e.g., relative to the sensor boards 49, 51. Accordingly, the estimated pose of the trocar 63 that is input to the deterministic model can be considered a selected pose (or initially, a guessed pose) of the trocar 63, and the deterministic model run by the processor produces, as an output, estimated sensor readings that correspond to this estimated pose of the trocar 63. In one variation, the estimated pose of the trocar 63 that is initially run through the deterministic model by the processor can be a stored set of values, e.g., predefined values, that can be based on typical trocar placements or arrangements that are known from historical data.

The estimated sensor readings produced by the processor from the deterministic model may be different from the measured sensor readings received by the processor from the sensor system 47 such that it can be desirable to reconcile the measured sensor readings with the estimated sensor readings, for example, to account for variables that may affect the accuracy of the measured sensor readings, such as magnetic fields generated by other trocars or other surgical equipment in the vicinity of the robotic arm 19, or other electromagnetic interference. Accordingly, the processor in the control tower 3 can compute a similarity measure in which the estimated sensor readings from the deterministic model are compared to the measured sensor readings from the sensor system 47, and can be optimized by the processor, e.g., iteratively updated to approach one another within a predetermined range or tolerance of error (see block 109 of FIG. 10).

At least blocks 115 through 123 of FIG. 11 illustrate the optimization algorithm of block 109 of FIG. 10, according to one aspect of the disclosure. The optimization algorithm can incorporate an Interior-Point Algorithm with Analytic Hessian, a non-linear least-squares solver, or a different optimization algorithm. An initial estimated or guessed pose of the trocar 63 (block 115) is run through the deterministic model by the processor to produce estimated sensor readings (block 117 in FIG. 11). These are then compared by the processor to the measured sensor readings received from the sensor system 47 (block 119), and the processor calculates whether the difference between the estimated sensor readings and the measured sensor readings is within an acceptable range or tolerance of error (block 121). If the difference between the estimated sensor readings and the measured readings are not within the acceptable range or tolerance of error, the processor adjusts the guessed or estimated pose of the trocar 63 (block 123) resulting in an updated estimated pose of the trocar 63 that is run through the deterministic model by the processor to produce updated estimated sensor readings (repeating block 117). The difference between the updated estimated sensor readings and the measured sensor readings is then calculated by the processor (repeating block 119) to determine whether the difference between the estimated sensor readings and the measured sensor readings are within the acceptable range or tolerance of error (repeating block 121.) If such difference is not within the acceptable range or tolerance of error, the estimated pose of the trocar 63 is iteratively updated again (repeating block 123) and run through the deterministic model by the processor. This iterative optimization algorithm continues until a set of optimized or final updated estimated sensor readings are produced by the processor that are within the acceptable range or tolerance of error (the "yes" branch at the output of block 121.)

The final updated estimated sensor readings produced through the aforementioned optimization correspond to a "determined pose" of the attachment portion 69 of the trocar 63, which, along with a pose of the docking interface 27, provides a transform that can be associated with a target or planned trajectory for guiding or driving the robotic arm 19, as described further herein. In this regard, via optimization by the processor of the estimated sensor readings produced through the deterministic model and the measured sensor readings received from the sensor system 47, the surgical robotic system 1 is operable to discriminate between the magnetic fields B1, B2 that are representative of the pose of the trocar 63 and other magnetic fields or electromagnetic interference such as those produced by other trocars or other surgical equipment in the operating arena. In one variation, in the presence of multiple trocars, the surgical robotic system 1 can be configured to target and initiate magnetic sensing and docking of a given docking interface with a nearest trocar, and distinguish between the magnetic field produced by the nearest trocar and the magnetic fields produced by other trocars.

In a further operation performed by the processor, the final updated estimated sensor readings, which corresponds to the determined pose of the attachment portion 69 of the trocar 63, are compared to the pose of the docking interface 27, e.g., to provide a transform that is used to guide the docking interface 27 toward the trocar 63 (block 111 in FIG. 10.) In one variation, the pose of the docking interface 27 can be a known value, for example, as determined through a log of prior movements of the robotic arm 19 by the robotic arm actuators 17 or various other sensors of the surgical robotic system 1, e.g., a gyroscope, accelerometer, position encoders, etc. In another variation, the pose of the docking interface 27 can be considered a geometric center from which the robotic arm 19 can be guided or driven to translate or rotate to approach the trocar 63. Accordingly, and as shown in FIG. 7, the processor in the control tower 3 can provide a set of guidance or driving control signals to the robotic arm actuators 17 based upon the final updated estimated sensor readings, to provide a tracking planned trajectory for the robotic arm 19 and to effect guidance or driving of robotic arm 19 to position and orient the docking interface 27 into docking facing relation with the attachment portion 69 of the trocar 63 such that the docking interface 27 matches or has substantially the same orientation as the orientation of the attachment portion 69 in a third or corrected entry position. It will be understood that, in the third or corrected entry position, the docking interface 27 is positioned proximate, but separate from, the trocar 63, and that the docking interface 27 is oriented such that only a final translational guidance of the robotic arm 19/docking interface 27 toward the trocar 63 will be sufficient to accomplish docking of the docking interface 27 with the trocar 63 (block 111). Two approaches for guiding the robotic arm 19 and in particular its tool drive and docking interface 27, toward the trocar 63 for docking are described further below in connection with FIG. 16A and FIG. 16B.

Position and/or Orientation Sensing of a Trocar Using a Machine Learning Model

A physical/mathematical model to estimate the pose of one or more magnets in a target (such as a trocar) is difficult to determine and may yield incorrect results due to sensor or signal noise, imprecise modelling, or other/unknown magnetic fields. In order to offer an alternative, or improve upon the above-presented surgical robotic system, a further surgical robotic system is described below in which a programmed processor makes the prediction or estimate of the trocar pose relative to the robot arm, by means of a machine learning model, e.g., an artificial neural network, or simply "neural network." The neural network is trained to predict the pose of the trocar, based on magnetic sensor readings such as in the embodiments described above. In one embodiment, this solution is deployed as the primary method for estimation of the trocar pose. In another embodiment, the neural network based solution is deployed in parallel with a deterministic model-based solution for pose estimation, which enables redundancy and therefore increases robustness of the docking procedure.

In various embodiments of a surgical robotic system described herein, a machine learning model is trained to perform regression analysis on the measured sensor readings (information obtained by the sensor readings) to thereby effectively estimate the pose of the trocar. The training process is performed offline, and may require a number of sensor measurements and corresponding known, ground truth pose data. The network is sufficiently trained when the change of the loss converges. To evaluate the performance of the machine learning model, pose is predicted (estimated) on a set of measurement data that has not been used for training and then the predicted pose is compared to the corresponding known ground truth pose to find out the error.

Figure 13:
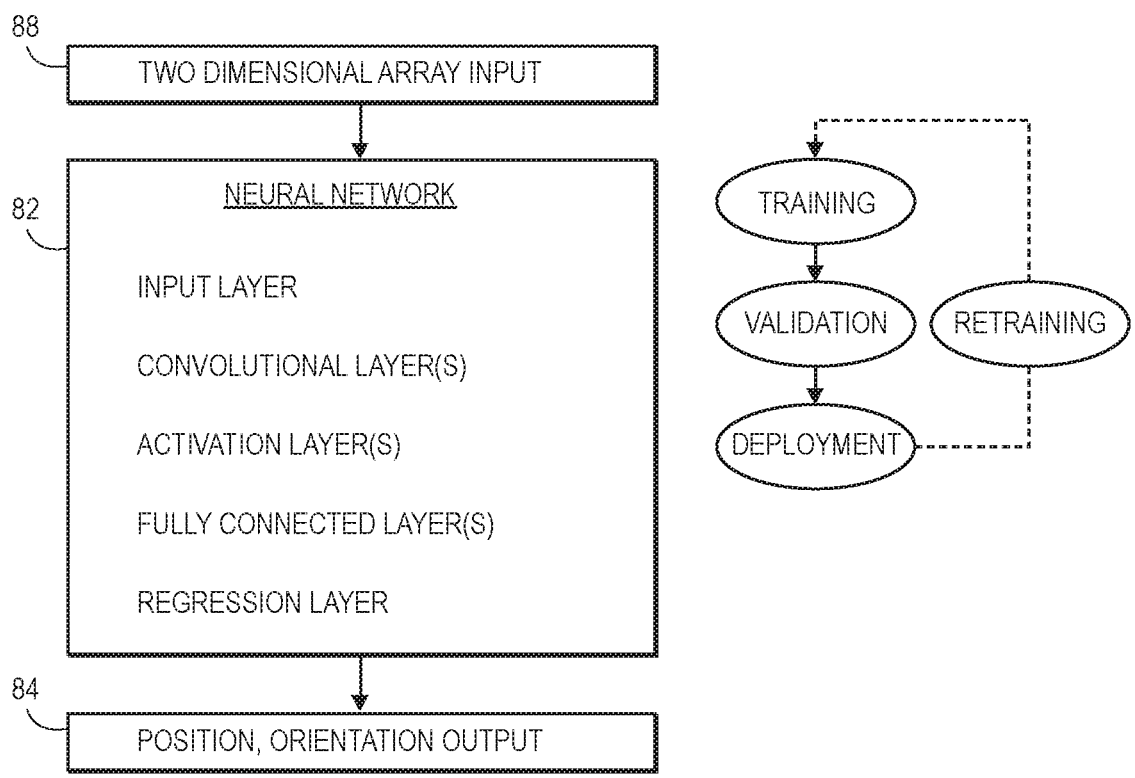
FIG. 13 illustrates some of the components of an example machine learning model suitable for embodiments of the surgical robotic system of FIG. 12.

The machine learning model can be deployed either as a primary algorithm to estimate the pose of the trocar, or as a redundancy measure in parallel with a physical/deterministic model. The machine learning model may have, for example, a simple architecture of a combination of input layer, multiple convolutional layers (+multiple rectified linear unit layer), one or more fully connected layers, and a regression output layer that enables the estimation of the pose of the arrangement of magnets. Note that in contrast to many classification or segmentation problems, the neural network here performs regression analysis upon the magnetic sensor measurements to result in a pose (position and orientation) of a trocar. This allows the machine learning model to estimate poses that were not part of the training data. FIG. 13 described further below illustrates an example machine learning model that can be used to estimate the position or orientation of a set of one or more magnets in a trocar.

Figure 12:
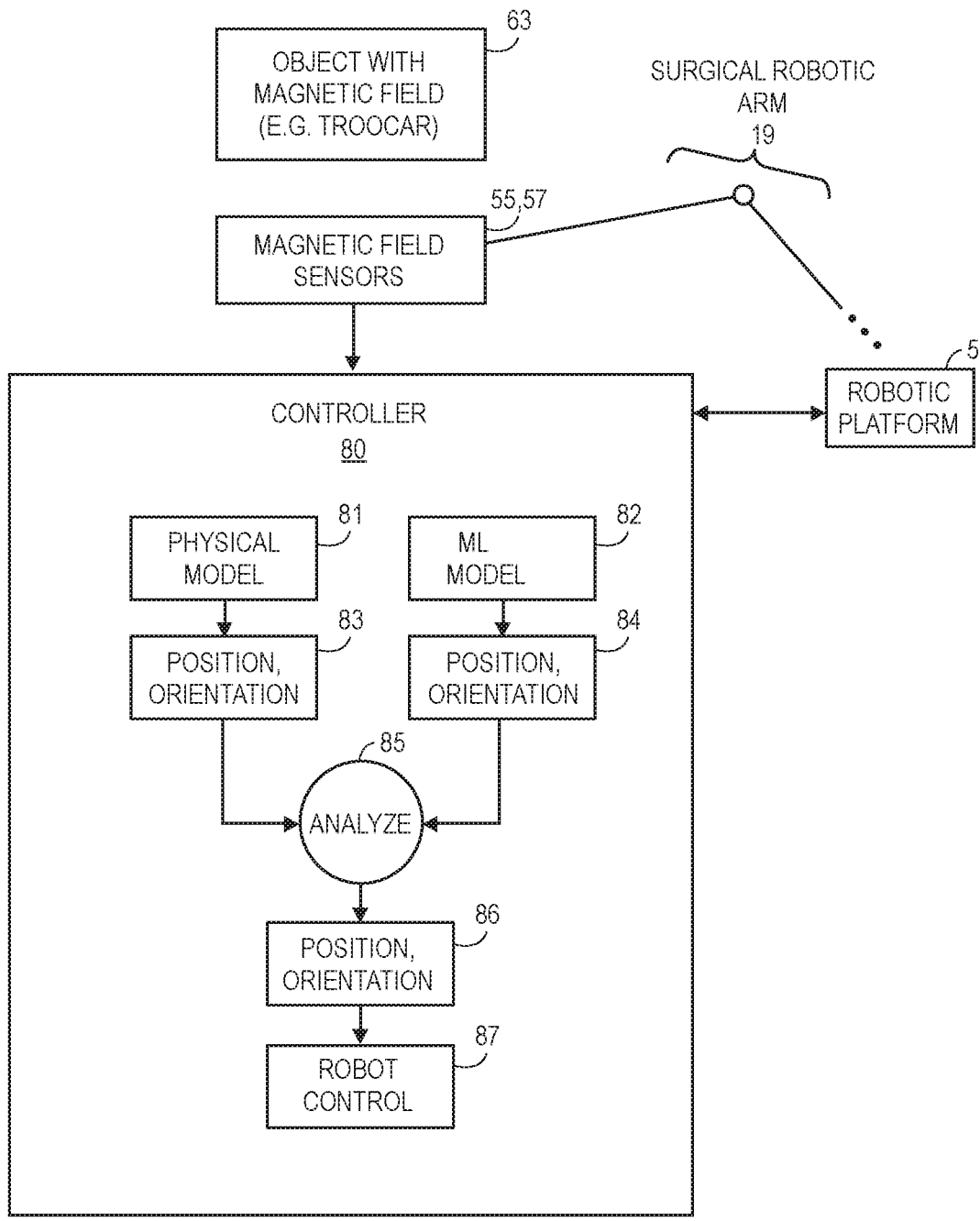
FIG. 12 is a block diagram of a surgical robotic system that uses magnetic field sensors, a physical model and a machine learning model to determine the pose of an object, for example a trocar that is magnetic, according to an aspect of the disclosure here.

To improve accuracy, the machine learning model can be used in parallel with a physical model. A comparison of the poses of the trocar estimated by the physical model and by the machine learning model allows the system to confirm the two pose estimates, reject a current set of magnetic sensor measurements, or combine the two pose estimates into a single, final pose estimate. FIG. 12 illustrates a controller 80 that performs such a comparison. The controller 80 as a programmed processor executes a process that obtains magnetic sensor measurements from several magnetic field sensors, and computes a physical model estimate 83 of the pose based on a physical model 81 and (in a parallel path) a machine learning model estimate 84 of the pose based on an evaluation of the sensor measurements through a trained machine learning model 82. After time synchronization is performed based on the timestamps of the sensor measurements (to ensure that the two estimates are referring to the same pose at a particular point in time), the two pose estimates are compared by an analyzer 85, which allows the system to either reject the pose estimates, or accept them and thereby update a final estimate 86 (position and orientation). The updated final estimate 86 is then used by a robotic arm to trocar docking control algorithm (robot control 86) that guides the robotic arm until the docking interface 27 of the arm 19 is ready to dock with the attachment portion trocar 63

Still referring to FIG. 12, in one embodiment the controller 80 (as part of a surgical robotic system) receives digital output measurements from the magnetic field sensors 55, 57 and has stored in microelectronic memory a physical model 81 (a stored data structure) and a machine learning model 82 (a stored data structure) which it uses to compute estimates of the pose of an object which is producing a magnetic field picked up by the sensor. The object, which can be for example the trocar 63—see FIG. 6—could have structural elements such as the flanged upper portion of head 67 and the attachment portion 69 that are made of magnetic material. As an alternative, or in addition, it could have two or more discretely or separately formed magnets that are attached to or embedded into a structural element. The magnetic field sensors 55, 57 could be arranged in an array as shown in FIG. 5, or in various further arrangements as readily devised in keeping with the teachings herein. The magnetic field sensors 55, 57 are attached to the surgical robotic arm 19. The arm 19 is attached to and is extending from the platform 5, or in further embodiments is attached to another robotic arm or, more generally to any base or other apparatus. The platform 5 can be fixed or mobile.

The controller 80 has one or more processors ("a processor") that executes instructions stored in memory, which include a physical model 81 that produces an estimate of the pose as described above with reference to FIG. 10 and FIG. 11. The memory also includes a machine learning model 82 such as an artificial neural network. Both the physical model and the machine learning model receive input from the magnetic field sensors 55, 57 and produce position and orientation information as estimates 83, 84 about the object, as a physical model estimate 83 and a machine learning model estimate 84 of the actual pose (position and orientation) of the object. The estimated position and orientation information from these two different paths are reconciled by an analyzer 85, which produces reconciled position and orientation information as a final estimate 86 for use by a robot control 86 in controlling the surgical robotic arm 19.

In one embodiment, the object is the trocar 63 with one or more magnets, and the magnetic field sensors 55, 57 are installed in the end effector and more specifically in the docking interface 27 (see, e.g., FIG. 2, FIG. 3 and FIG. 4) attached to the surgical robotic arm 19. The controller 80 automatically docks the docking interface of the surgical robotic arm to the trocar, using the position and orientation information of the estimates 83, 84 and of the final estimate 86. In one aspect, the surgical robotic system just has the machine learning model 82 to compute the estimate 84 which may be analyzed to result in the final estimate 86, without relying on any estimate produced by the physical model 81.

As examples of how the analyzer 85 reconciles position and orientation information of the estimates 83, 84, consider various possibilities. The analyzer 85 can monitor position and orientation information estimate 83 from the physical model 81 and position and orientation information estimate 84 from the machine learning model 82, and compare the two. If one or the other path is producing an anomalous reading, this can be deduced by the analyzer 85, which would then pass along what is considered the more accurate values as the position and/or orientation information, in the final estimate 86 of the pose, to the robot control 134. The analyzer 85 could look for smoothly varying position and/or orientation information 83, 84 from the two paths, and recognize when one set of values deviates sharply or erratically from the other. The analyzer 85 could perform averaging of the position and/or orientation information 83, 84 from the two paths, or select one or the other set of position and/or orientation information 83, 84, rejecting the other or using the other as a cross check.

FIG. 13 illustrates the example where the machine learning model 82 is a convolutional neural network. Other types of neural networks may be suitable for further embodiments. The convolutional neural network has an input layer, which receives a two-dimensional array input 88 of measurements from the magnetic field sensors 55, 57 (see FIG. 5 and FIG. 12). One or more convolutional layers, one or more activation layers, and one or more fully connected layers propagate from one layer to another and produce classification scores. A regression layer analyzes these classification scores to produce position and/or orientation information as machine learning model estimate 84.

The convolutional neural network undergoes training, followed by validation and then deployment into a functioning system, such as the surgical robotic system described here. Optionally, retraining can be performed. For example, the convolutional neural network could be retrained if there is a change in the magnetic field produced by the object. This could occur for instance if the trocar 63 is replaced with a different trocar, or it could occur if one or more magnets are added to the trocar 63, or if one or magnets are moved (repositioned) or removed. In an embodiment where the trocar's structural element itself is magnetized (to be detected by the magnetic sensors on the robotic arm 19), it could be that over time the magnetic field changes and therefore necessitates retraining of the convolutional neural network.

To train the machine learning model, training data is required that comprises sensor measurements and ground truth poses. In one embodiment described above with reference to FIG. 12, magnets are attached to a trocar, magnetic field sensors are attached to a robot end-effector, and a large number of samples covering the entire workspace and entire range of rotations of each of many positions are obtained. This dataset is used to train the machine learning model, by optimizing the weights for each node in the network graph.

Experimental results for one embodiment indicate that the machine learning model performs with a similar accuracy as a physical model (e.g., mean norm error of 1.7 mm), while the duration of evaluation is significantly lower. The physical model converges within 20-100 ms, while the machine learning model provides results within 0.1-8 ms on the same computer.

FIG. 14 illustrates a two-dimensional physical array of sensors and a two-dimensional array of neural network input elements 88, which are suitable for use in the convolutional neural network of FIG. 13 and the surgical robotic system of FIG. 12. Various arrangements of sensor signals as input to a machine learning model are possible, and they are not limited to the specific arrangements described herein. It has been found advantageous to arrange output data from the magnetic field sensors 55, 57 into a two-dimensional array of elements, for input to the convolutional neural network. The neural network may also be optimized as for image recognition for example as if the two-dimensional array of neural network input elements 88 were a digital image produced by a camera (e.g., a series of images forming video.) It has been found as further advantageous to arrange the output data from the magnetic field sensors 55, 57 in a non-adjacent manner, or even a random manner for input to the neural network 82, as described below or in a variation thereof.

The embodiment depicted in FIG. 14 should be considered an example and not limiting as to numbers of sensors, type of sensor, number of output data elements per sensor, and arrangement of sensor output data in a two-dimensional physical array. See for example, the array of sensors 55, 57 depicted in FIG. 5. Each sensor, e.g., of magnetic field sensors 55, 57 labeled sensor 1, sensor 2, etc., senses magnetic field in each of three orthogonal directions, and is of a type commonly known as an XYZ or three axis magnetic field sensor. Here, these magnetic field sensors are depicted as each sensing and producing signals for B0, B1 and B2 magnitudes of the magnetic field vector at the location of the sensor. The two-dimensional array of neural network inputs contains output data from the sensors (in the two-dimensional physical array) arranged at random, as a specific example of the two-dimensional array input for the convolutional neural network in FIG. 13. Output data from adjacent magnetic field sensors in the two-dimensional physical array are non-adjacent elements in the two-dimensional array of neural network inputs. Or, adjacent elements in the two-dimensional array of neural network inputs 88 are from nonadjacent magnetic field sensors in the two-dimensional physical array of sensors. So, for example, the magnetic field sensors labeled sensor 1 and sensor 2 are adjacent in the two-dimensional physical array, but their output data are nonadjacent in the two-dimensional array of neural network inputs. And, the output data of sensor 12 and sensor 3 are adjacent in the two-dimensional array of neural network inputs 88, but sensor 12 is not adjacent to sensor 3 in the two-dimensional physical array. Various further arrangements of sensors and inputs to the neural network with this principle of non-adjacency are readily devised. It should be appreciated that arrangements and rearrangements of sensors and their output data as inputs to the neural network 82 can be accomplished with sensor position changes, circuitry or wiring changes and/or with software or programming changes. Non-adjacency could even be extended to the individual signals from a given sensor, in arrangements for the neural network inputs.

Figure 15:
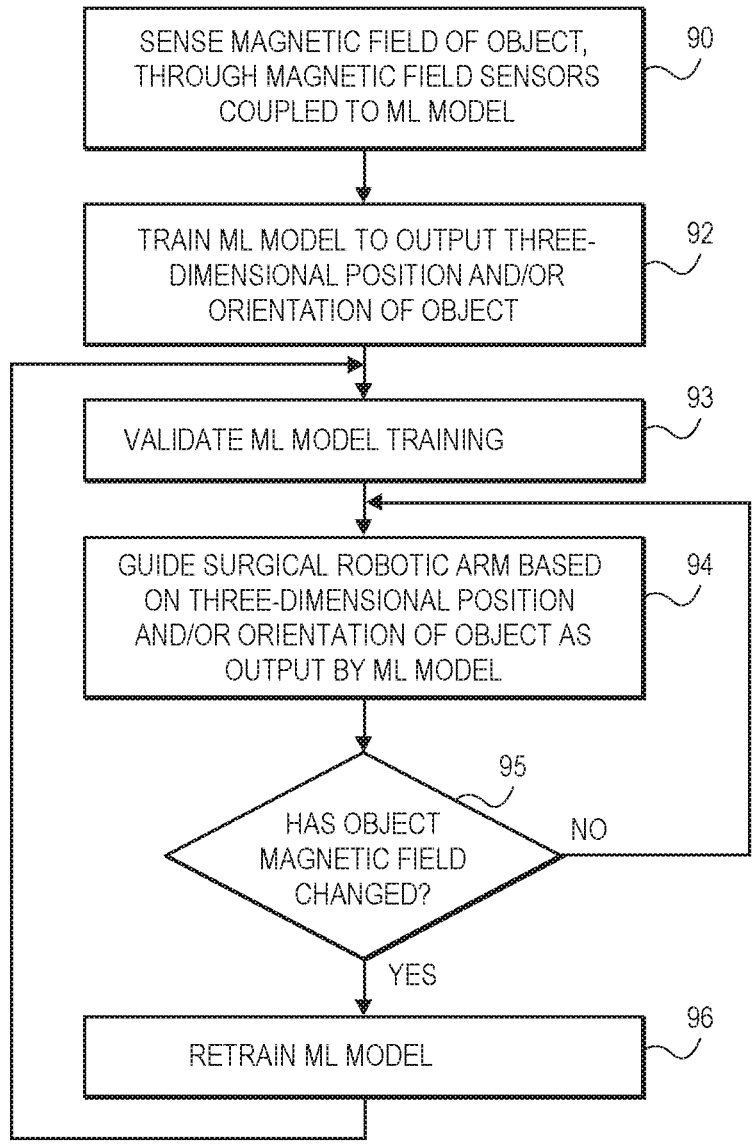
FIG. 15 is a process flow of a method of sensing position and/or orientation of an object, which can be performed by embodiments of the surgical robotic system of FIG. 12 and variations thereof.

FIG. 15 is a process flow of a method of sensing position and/or orientation of an object, which can be performed by embodiments of the surgical robotic system of FIG. 12 and variations thereof. In various embodiments, various objects that have a magnetic field can be used. The trocar 63 with a magnetic field can be used as the object. An objective of one version is to dock the docking interface 27 of the surgical robotic arm 19 to the trocar 63, where the trocar has a magnetic field and the docking interface has magnetic field sensors.

In an action 90, the magnetic field of the object is sensed through magnetic field sensors coupled to a machine learning model. The magnetic field sensors are attached to a surgical robotic arm, or more generally a robotic arm.

In an action 92, the machine learning model is trained to output three-dimensional position and/or orientation of the object. Examples of machine learning models and training are described above.

In an action 93, the machine learning model training is validated. Generally, this involves testing various positions and orientations of the object and verifying accuracy of the three-dimensional position and/or orientation information output by the machine learning model.

In an action 94, the surgical robotic arm is guided, based on the three-dimensional position and/or orientation of the object as output by the machine learning model. In embodiments where the object is a trocar with a magnetic field, the surgical robotic arm is guided automatically to dock the surgical robotic arm to the trocar.

In an action 95, it is determined whether there is a change in the object magnetic field. For example, the object could have aged and so its magnetic field is decreased, or one or more magnets of the object were added, removed, repositioned, etc. If the answer is no, there is no change to the magnetic field of the object, flow returns to the action 94 in order to continue moving the surgical robotic arm. If the answer is yes, in that the object magnetic field has changed, then flow proceeds to the action 96, to retrain the machine learning model, and proceeds from there to the action 93 to validate the machine learning model training. Other branches are possible, such as other operations of the surgical robotic arm, or pausing or redirecting the surgical robotic system.

An aspect of the disclosure here is a method for training a machine learning model to output 3D position and 3D orientation of a trocar. The output 3D pose is to be used by an automated process that controls a surgical robotic arm for docking the arm to the trocar, for example while a tool drive is coupled to the arm and that has a docking interface in which there are a number of magnetic field sensors. The machine learning model may be trained to perform regression analysis on the measured sensor readings (information obtained by the sensor readings) to thereby effectively estimate the pose of the trocar. The training process is performed offline, and may require a number of sensor measurements and corresponding known, ground truth pose data. The ML model is sufficiently trained when the change of the loss converges. To evaluate the performance of the trained machine learning model, the model is asked to predict (estimate) a pose based on an input set of measurement data that has not been used for training. This predicted pose is then compared to the corresponding known ground truth pose to find out the error.

The machine learning model may be a convolutional neural network configured for propagating an input two-dimensional array of output data from the magnetic field sensors. In one aspect, the neural network comprises: an input layer arranged to receive the input two dimensional array of output data from the magnetic field sensors; a plurality of convolutional layers; one or more fully connected layers; and a regression output layer to output the three-dimensional position or three-dimensional orientation.

In another aspect, the machine learning model is a convolutional neural network arranged to receive the input as a two-dimensional array of output data from magnetic field sensors, and wherein output data of adjacent magnetic field sensors, of the plurality of magnetic field sensors, are arranged as nonadjacent elements in the two-dimensional array of output data.

Guidance of the Robotic Arm for Docking

Once the pose of the trocar 63 has been determined (estimated), the robotic arm 19 is guided to dock with the trocar 63. Several approaches are possible for doing so in a way that makes it easier for a user or operator. In one aspect of the disclosure, as referred to by block 111 of FIG. 10, the processor in the control tower 3 can activate the robotic arm actuators 17 to guide or drive the robotic arm 19 according to a transformation matrix that relates the final estimate of the trocar pose to the present pose of the docking interface 27. Thus, the docking interface 27 is guided or driven toward the determined position and orientation of the trocar 63. Such guidance may be fully automatic or it may assist an operator's manual forcing of the arm 19 along a planned trajectory by way of producing a virtual spring that urges the arm back to the planned trajectory. This driving or guidance of the robotic arm 19 may include re-positioning of the docking interface 27 (according to the transform), and in some instances re-orienting the docking interface 27 (according to the transform) to achieve a corrected entry pose so as to be ready to dock with the attachment portion 69 of the trocar 63. Such guidance can be affected by the processor in the following two ways.

Figure 16A:
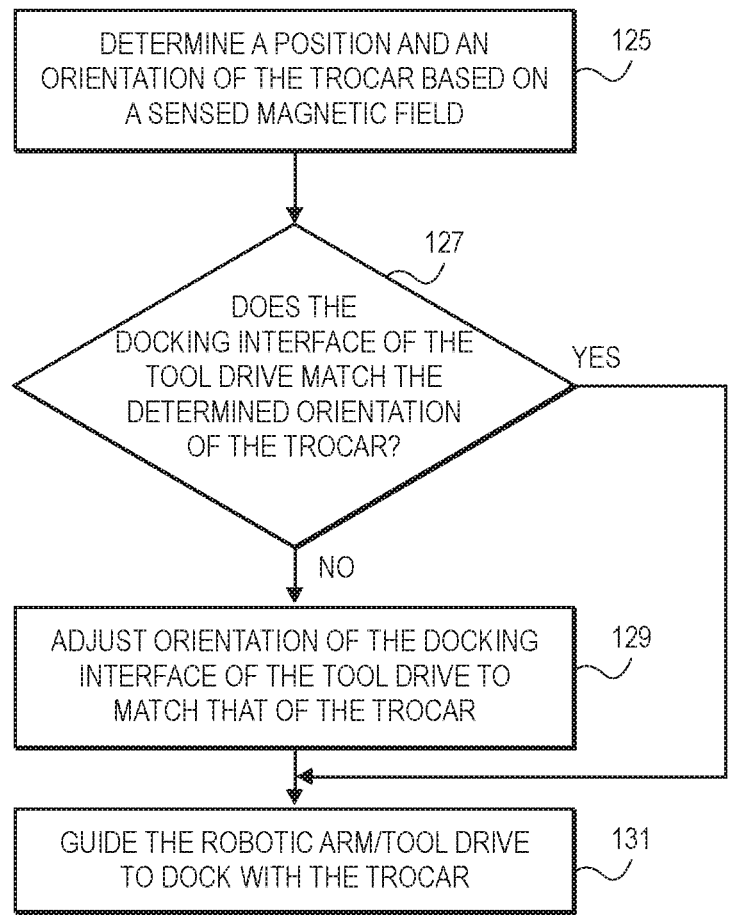
FIG. 16A is a process flow of a method for docking a tool drive attached to a robotic arm of a surgical robotic system to a trocar according to one aspect of the disclosure.

FIG. 16A (in conjunction with FIG. 7 and FIG. 8) illustrates the situation where during guidance or driving of the robotic arm 19 by the robotic arm actuators 17 (once the pose of trocar has been determined in block 125), the processor guides the arm 19 until the position of the docking interface 27 is close to, but not ready to dock with, the attachment portion 69 of the trocar 63. During this guidance, the orientation of the docking interface 27 may remain fixed. When the processor detects that the position of the docking interface 27 is close enough to the attachment portion 29, or has reached a so-called "entry pose", the processor then checks whether the orientation of the docking interface 27 matches that of the entry pose, i.e. whether the determined orientation of the docking interface 27 matches the estimated orientation of the trocar 63 (block 127). If the processor determines that the docking interface 27 does not match the orientation of the trocar 63, the processor controls the robotic arm actuators 17 to further drive or guide the robotic arm 19 so as to re-orient the docking interface 27 to match that of the trocar 63 (block 129). Once the determined orientation of the docking interface 27 matches the estimated orientation of the trocar 63, such that the docking interface 27 is now in its "corrected entry pose", the processor drives the robotic arm actuators 17 so as to move the docking interface 27 into the ready to dock position with the attachment portion 69 of the trocar, e.g., only in a translation movement and without having to now change the orientation of the docking interface 27 (block 131.) The tool drive 23 is now ready to dock with the trocar 63.

Figure 16B:
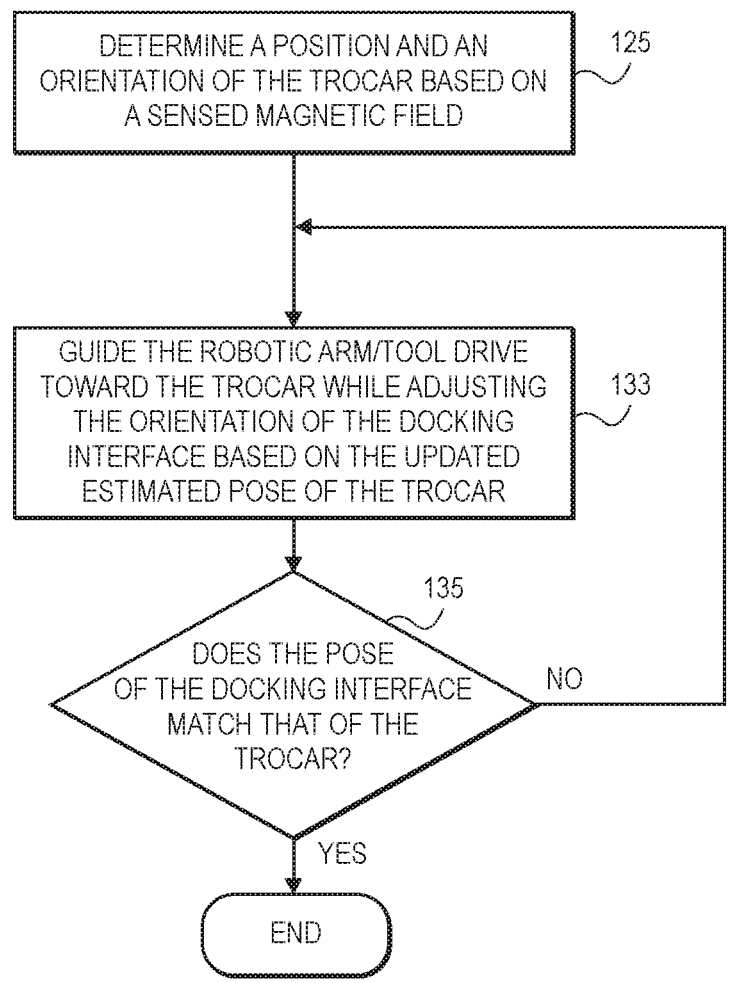
FIG. 16B is a process flow of a method for docking a tool drive attached to a robotic arm of a surgical robotic system to a trocar according to another aspect of the disclosure.

FIG. 16B (in conjunction with FIG. 7 and FIG. 8) serves to illustrate another docking process for the tool drive 23, where here both the orientation and the position of the docking interface 27 are being adjusted automatically by the processor while the robotic arm 19 is guided towards the trocar (block 133.) The process is otherwise similar to FIG. 16A in that it too begins with block 125 in which the pose of the trocar is estimated (determined by the processor) as described above. In contrast to FIG. 16A however, here the processor is repeatedly or continually checking the full pose of the docking interface 27 against the estimated pose of the trocar 63 while the arm 19 is being guided toward the trocar, and in response adjusting as needed both the position and the orientation of the docking interface 27. For example, the orientation of the docking interface 27 is thus maintained at all times (while the docking interface 27 moves toward the trocar) to match the estimated orientation of the attachment portion 69 of the trocar. This process continues or loops as shown, until block 135 reveals that the pose of the docking interface 27 matches the estimated pose of the trocar, at which the docking interface 27 is ready to dock.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

The invention claimed is:

1. A surgical robotic system for sensing pose, the system comprising:
   a surgical robotic arm;
   a plurality of magnetic field sensors coupled to the surgical robotic arm; and
   a machine learning model coupled to the plurality of magnetic field sensors and trained to output an estimate of a pose of a trocar that is producing a magnetic field, based on output data from the plurality of magnetic field sensors.

2. The surgical robotic system of claim 1, wherein the machine learning model is a convolutional neural network configured for image processing of an input two-dimensional array of output data from the magnetic field sensors.

3. The surgical robotic system of claim 1, further comprising the trocar having one or more discrete magnets attached thereto that produce the magnetic field.

4. The surgical robotic system of claim 1 wherein output data from the plurality of magnetic field sensors are arranged in a two-dimensional array as input to the machine learning model.

5. The surgical robotic system of claim 1, further comprising:
   a controller having a physical model that describes how the magnetic field sensors can sense a magnetic field produced by one or magnets, the controller configured to guide the surgical robotic arm to dock with the trocar based on i) a physical model estimate of the pose of the trocar produced using the physical model and ii) a machine learning model estimate of the pose of trocar produced using the machine learning model.

6. The surgical robotic system of claim 1, further comprising:
a tool drive coupled to the surgical robotic arm, wherein the plurality of magnetic field sensors and a docking interface are located on a base of the tool drive, and wherein the docking interface is configured to receive an attachment portion of the trocar.

7. The surgical robotic system of claim 6, wherein:
the plurality of magnetic field sensors are arranged in two or more physical arrays that are spaced apart from each other;
the machine learning model is arranged to receive input from the plurality of magnetic field sensors as a two-dimensional array of sensor measurements; and
wherein adjacent elements in the two-dimensional array that are input to the machine learning model are from nonadjacent magnetic field sensors in the two or more physical arrays.

8. The surgical robotic system of claim 1, wherein:
the plurality of magnetic field sensors is arranged in two or more physical arrays;
the machine learning model is arranged to receive input from the plurality of magnetic field sensors as a two-dimensional array of sensor measurements; and
wherein adjacent elements in the two-dimensional array that are input to the machine learning model are from nonadjacent magnetic field sensors in the two or more physical arrays.

9. A surgical robotic system, comprising:
a surgical robotic arm;
a tool drive coupled to the arm and having a docking interface that comprises a plurality of magnetic field sensors; and
a programmed processor that implements i) a machine learning model which outputs three-dimensional position and three-dimensional orientation of a trocar as a machine learning model estimate of a pose of the trocar, based on input to the machine learning model from the plurality of magnetic field sensors, ii) a physical model of a magnetic field system wherein the magnetic field system comprises i) a magnetic field produced by a magnetic trocar and ii) the plurality of magnetic field sensors, wherein the physical model produces a physical model estimate of the pose of the trocar, and wherein the processor produces a final estimate of the pose of the trocar based on the machine learning model estimate and based on the physical model estimate, and iii) a robot control algorithm for guiding the surgical robotic arm based on the final estimate of the pose until the docking interface is ready to dock with the trocar.

10. The surgical robotic system of claim 9, wherein the machine learning model is a convolutional neural network configured for propagating an input two-dimensional array of output data from the magnetic field sensors, and the neural network comprises:
an input layer arranged to receive the input two dimensional array of output data from the magnetic field sensors;
a plurality of convolutional layers;
one or more fully connected layers; and
a regression output layer to output the three-dimensional position or three-dimensional orientation.

11. The surgical robotic system of claim 9, wherein the machine learning model is a convolutional neural network arranged to receive the input as a two-dimensional array of output data from magnetic field sensors, and wherein output data of adjacent magnetic field sensors, of the plurality of magnetic field sensors, are arranged as nonadjacent elements in the two-dimensional array of output data.

12. The surgical robotic system of claim 9, further comprising:
a controller coupled to the plurality of magnetic field sensors and the surgical robotic arm, the controller configured to use both a physical model and the machine learning model for redundant estimation of the three-dimensional position or three-dimensional orientation.

13. A method for sensing position or orientation of a trocar by a surgical robotic system, the method comprising:
sensing, with a plurality of magnetic field sensors attached to a surgical robotic arm of the surgical robotic system, a magnetic field produced by the trocar;
providing as an input of a machine learning model sensed data from the plurality of magnetic field sensors, and wherein the machine learning model is configured to output a first estimate of three-dimensional position or three-dimensional orientation of the trocar; and
guiding by the surgical robotic system the surgical robotic arm to the trocar, based on the first estimate of three-dimensional position or three-dimensional orientation of the trocar as output by the machine learning model.

14. The method of claim 13 further comprising:
signaling by the surgical robotic system that the surgical robotic arm is ready to dock with the trocar, in response to determining that a pose of a docking interface attached to the arm matches an estimated three-dimensional position and an estimated three-dimensional orientation of the trocar as output by the machine learning model.

15. The method of claim 13, further comprising:
re-training the machine learning model, responsive to determining that the magnetic field produced by the trocar has changed.

16. The method of claim 13, further comprising:
producing a second estimate of three-dimensional position or three-dimensional orientation of the trocar using a physical model whose input is the sensed data from the plurality of magnetic field sensors, wherein the sensed data from the magnetic field sensors is also used by the machine learning model to output the first estimate; and
determining whether the second estimate is at fault, based on the first estimate.

17. The method of claim 16 further comprising:
producing a final estimate of three-dimensional position or three-dimensional orientation of the trocar responsive to determining whether the second estimate is at fault, wherein the guiding the surgical robotic arm is based on the final estimate.

18. The method of claim 13, further comprising:
arranging the sensed data from adjacent ones of the plurality of magnetic field sensors as non-adjacent elements of a two dimensional array that is input to the machine learning model.

* * * * *